US011911272B2

(12) United States Patent
Chan et al.

(10) Patent No.: US 11,911,272 B2
(45) Date of Patent: Feb. 27, 2024

(54) BIOABSORBABLE MEDICAL DEVICES

(71) Applicant: W. L. Gore & Associates, Inc., Newark, DE (US)

(72) Inventors: Michael C. Chan, Flagstaff, AZ (US); Edward H. Cully, Newark, DE (US); Jeffrey B. Duncan, Flagstaff, AZ (US); Byron K. Hayes, Flagstaff, AZ (US); Samuel Joynson, Flagstaff, AZ (US); Tom R. McDaniel, Flagstaff, AZ (US); David J. Messick, Flagstaff, AZ (US); Edward E. Shaw, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 0 days.

(21) Appl. No.: 16/745,831

(22) Filed: Jan. 17, 2020

(65) Prior Publication Data
US 2020/0229924 A1 Jul. 23, 2020

Related U.S. Application Data

(60) Provisional application No. 62/794,312, filed on Jan. 18, 2019.

(51) Int. Cl.
*A61B 17/03* (2006.01)
*A61B 17/00* (2006.01)
(Continued)

(52) U.S. Cl.
CPC ........ *A61F 2/2439* (2013.01); *A61B 17/0057* (2013.01); *A61F 2/2409* (2013.01);
(Continued)

(58) Field of Classification Search
CPC ...... A61F 2/2409; A61F 2/2439; A61L 27/58; A61B 17/0057; A61B 2017/00575; A61B 2017/00597
See application file for complete search history.

(56) References Cited

U.S. PATENT DOCUMENTS 2,867,807 A 1/1959 Anstett
3,868,956 A 3/1975 Alfidi et al.
(Continued)

FOREIGN PATENT DOCUMENTS

AU 2017228585 A1 10/2017
CN 101426454 A 5/2009
(Continued)

OTHER PUBLICATIONS

International Preliminary Report on Patentability received for PCT Patent Application No. PCT/US2013/063862, dated May 7, 2015, 8 pages.
(Continued)

*Primary Examiner* — Dinah Baria

(57) ABSTRACT

Various aspects of the present disclosure are directed toward apparatuses, systems, and methods that include a plurality of absorbable filaments arranged in a support structure and configured degrade within a defined time period and a membrane arranged about the plurality of absorbable filaments and configured to contain fragments of the plurality of absorbable filaments in response to a fracture or degradation of a filament.

32 Claims, 26 Drawing Sheets

(51) Int. Cl.
*A61F 2/24* (2006.01)
*A61L 27/58* (2006.01)

(52) U.S. Cl.
CPC ..... *A61L 27/58* (2013.01); *A61B 2017/00575* (2013.01); *A61B 2017/00597* (2013.01)

(56) References Cited

U.S. PATENT DOCUMENTS

| | | |
|---|---|---|
| 4,886,062 A | 12/1989 | Wiktor |
| 5,575,816 A | 11/1996 | Rudnick et al. |
| 5,626,611 A | 5/1997 | Liu et al. |
| 5,676,685 A | 10/1997 | Razavi |
| 5,735,892 A | 4/1998 | Myers et al. |
| 5,836,962 A | 11/1998 | Gianotti |
| 5,944,738 A | 8/1999 | Amplatz et al. |
| 6,309,414 B1 | 10/2001 | Rolando et al. |
| 6,315,788 B1 | 11/2001 | Roby |
| 6,719,782 B1 | 4/2004 | Chuter |
| 7,344,563 B2 | 3/2008 | Vallana et al. |
| 7,420,124 B2 | 9/2008 | Michael et al. |
| 7,500,376 B2 | 3/2009 | Bathurst et al. |
| 7,501,579 B2 | 3/2009 | Michael et al. |
| 7,651,523 B2 | 1/2010 | Eller |
| 7,740,653 B1 | 6/2010 | Pollock et al. |
| 7,780,686 B2 | 8/2010 | Park et al. |
| 7,799,070 B2 | 9/2010 | Bates et al. |
| 7,857,842 B2 | 12/2010 | Chuter |
| 8,024,851 B2 | 9/2011 | Barr et al. |
| 8,109,946 B2 | 2/2012 | Cahill et al. |
| 8,585,753 B2 | 11/2013 | Scanlon et al. |
| 8,663,308 B2 | 3/2014 | Schafer et al. |
| 9,017,350 B2 | 4/2015 | Karabey et al. |
| 9,861,467 B2 | 1/2018 | Cully et al. |
| 9,877,726 B2 | 1/2018 | Liu et al. |
| 9,943,315 B2 | 4/2018 | Kaplan et al. |
| 2003/0045898 A1 | 3/2003 | Harrison et al. |
| 2003/0105511 A1 | 6/2003 | Welsh et al. |
| 2003/0139819 A1 | 7/2003 | Beer et al. |
| 2003/0153972 A1 | 8/2003 | Helmus |
| 2004/0106978 A1 | 6/2004 | Greenberg et al. |
| 2004/0230288 A1 | 11/2004 | Rosenthal |
| 2005/0043759 A1 | 2/2005 | Chanduszko |
| 2005/0119690 A1 | 6/2005 | Mazzocchi et al. |
| 2005/0288775 A1 | 12/2005 | Dong |
| 2006/0147612 A1 | 7/2006 | Da Rocha Loures |
| 2006/0224234 A1 | 10/2006 | Jayaraman |
| 2006/0287707 A1 | 12/2006 | Roeder et al. |
| 2007/0173923 A1 | 7/2007 | Savage et al. |
| 2007/0244518 A1* | 10/2007 | Callaghan .......... A61B 17/0057 606/215 |
| 2008/0077180 A1* | 3/2008 | Kladakis ............ A61B 17/0057 606/216 |
| 2008/0082162 A1 | 4/2008 | Boismier et al. |
| 2008/0177376 A1 | 7/2008 | Krivoruchko et al. |
| 2008/0208325 A1 | 8/2008 | Helmus et al. |
| 2009/0187240 A1 | 7/2009 | Clerc et al. |
| 2009/0240323 A1 | 9/2009 | Wilcox |
| 2009/0260852 A1 | 10/2009 | Schaffer |
| 2009/0275963 A1 | 11/2009 | May et al. |
| 2009/0275974 A1 | 11/2009 | Marchand et al. |
| 2009/0320435 A1 | 12/2009 | Bertsch et al. |
| 2010/0075168 A1 | 3/2010 | Schaffer |
| 2010/0107628 A1 | 5/2010 | Schaffer |
| 2010/0114148 A1 | 5/2010 | Albrecht et al. |
| 2010/0262228 A1 | 10/2010 | Udipi et al. |
| 2011/0071619 A1 | 3/2011 | Bliss et al. |
| 2011/0112626 A1 | 5/2011 | Van Der Leest |
| 2011/0135806 A1 | 6/2011 | Grewe et al. |
| 2011/0144669 A1 | 6/2011 | Becking et al. |
| 2011/0313271 A1 | 12/2011 | Schulman |
| 2011/0319977 A1 | 12/2011 | Pandelidis et al. |
| 2011/0319978 A1 | 12/2011 | Schaffer |
| 2012/0029619 A1 | 2/2012 | Schroeder |
| 2012/0109199 A1 | 5/2012 | Kothari et al. |
| 2012/0143227 A1 | 6/2012 | Steckel et al. |
| 2012/0283811 A1 | 11/2012 | Neilan |
| 2012/0303112 A1 | 11/2012 | Armstrong et al. |
| 2013/0127094 A1 | 5/2013 | Dave |
| 2013/0261735 A1 | 10/2013 | Pacetti et al. |
| 2013/0296925 A1* | 11/2013 | Chanduszko ........ A61B 17/0057 606/213 |
| 2014/0107399 A1 | 4/2014 | Spence |
| 2014/0120324 A1 | 5/2014 | Cully |
| 2014/0277576 A1 | 9/2014 | Landgrebe et al. |
| 2014/0356407 A1 | 12/2014 | Mangiardi |
| 2015/0039017 A1* | 2/2015 | Cragg .............. A61B 17/12031 606/200 |
| 2015/0151027 A1 | 6/2015 | Zhang et al. |
| 2015/0182674 A1 | 7/2015 | Schaffer |
| 2016/0128849 A1 | 5/2016 | Yan et al. |
| 2016/0138148 A1 | 5/2016 | Schaffer et al. |
| 2016/0151610 A1 | 6/2016 | Schaffer |
| 2016/0199621 A1 | 7/2016 | Schaffer |
| 2016/0228233 A1 | 8/2016 | Winkler et al. |
| 2016/0248988 A1 | 8/2016 | Urfalioglu et al. |
| 2016/0249899 A1* | 9/2016 | Cahill ................ A61B 17/0057 606/215 |
| 2017/0079662 A1 | 3/2017 | Rhee et al. |
| 2017/0119936 A1 | 5/2017 | Schaffer et al. |
| 2017/0135801 A1 | 5/2017 | Delaney et al. |
| 2018/0125630 A1 | 5/2018 | Hynes et al. |
| 2018/0209073 A1 | 7/2018 | Ganatra et al. |
| 2020/0121441 A1 | 4/2020 | Taylor et al. |
| 2020/0229953 A1 | 7/2020 | Cully et al. |

FOREIGN PATENT DOCUMENTS

| | | |
|---|---|---|
| CN | 102711677 A | 10/2012 |
| EP | 0806190 A1 | 11/1997 |
| EP | 1066804 A2 | 1/2001 |
| EP | 0888093 B1 | 7/2001 |
| EP | 1049421 B1 | 1/2005 |
| EP | 1919532 A2 | 5/2008 |
| EP | 2056751 B1 | 4/2011 |
| EP | 2968664 A1 | 1/2016 |
| EP | 2968690 A1 | 1/2016 |
| EP | 3297541 A1 | 3/2018 |
| JP | 2002-502625 A | 1/2002 |
| JP | 2002-530146 A | 9/2002 |
| JP | 2007-523686 A | 8/2007 |
| JP | 2008-546452 A | 12/2008 |
| JP | 2010-501274 A | 1/2010 |
| JP | 2010-269161 A | 12/2010 |
| JP | 2016-052602 A | 4/2016 |
| JP | 2016-526438 A | 9/2016 |
| WO | 88/07774 A1 | 10/1988 |
| WO | 99/39646 A1 | 8/1999 |
| WO | 00/30563 A1 | 6/2000 |
| WO | 02/13725 A1 | 2/2002 |
| WO | 2005/006990 A2 | 1/2005 |
| WO | 2006/108065 A2 | 10/2006 |
| WO | 2006/138548 A1 | 12/2006 |
| WO | 2007/027251 A2 | 3/2007 |
| WO | 2008/024712 A2 | 2/2008 |
| WO | 2009/152376 A1 | 12/2009 |
| WO | 2011/042810 A2 | 4/2011 |
| WO | 2014/143521 A1 | 9/2014 |
| WO | 2014/210263 A1 | 12/2014 |
| WO | 2016/187575 A1 | 11/2016 |
| WO | 2018/053352 A1 | 3/2018 |
| WO | 2020/150558 A1 | 7/2020 |

OTHER PUBLICATIONS

International Search Report and Written Opinion received for PCT Patent Application No. PCT/US2013/063862, dated Dec. 5, 2013, 11 pages.

Zhu et al., Research Article, Animal Experimental Study of the Fully Biodegradable Atrial Septal Defect (ASD) Occluder, Journal of Biomedicine and Biotechnology, vol. 2012, Article ID 735989, 2012, 10 pages.

(56) References Cited

OTHER PUBLICATIONS

International Preliminary Report on Patentability received for PCT Patent Application No. PCT/US2020/014001, dated Jul. 29, 2021, 11 pages.
International Search Report and Written Opinion received for PCT Patent Application No. PCT/US2020/014001, dated Apr. 6, 2020, 15 pages.
International Preliminary Report on Patentability received for PCT Patent Application No. PCT/US2020/014002, dated Jul. 29, 2021, 8 pages.
International Search Report and Written Opinion received for PCT Patent Application No. PCT/US2020/014002, dated Apr. 8, 2020, 14 pages.

* cited by examiner

BIOABSORBABLE MEDICAL DEVICES

CROSS-REFERENCE TO RELATED APPLICATION

This application claims the benefit of Provisional Application No. 62/794,312, filed Jan. 18, 2019, which is incorporated herein by reference in its entirety for all purposes.

FIELD

The disclosure generally relates to implantable medical devices. More specifically, the disclosure is generally directed toward implantable medical devices that are absorbable, in whole or in part, for repair of cardiac and vascular defects or tissue openings, such as a patent foramen ovale (PFO) or shunt in the heart, the vascular system, or other location within a patient.

BACKGROUND

Occluding device implantation by open-heart surgery has historically been used to treat cardiac defects or tissue openings. More recently, to avoid the trauma and complications associated with open-heart surgery, a variety of trans-catheter closure techniques have been developed. In such techniques, an occluding device is delivered through a catheter to the site of the opening or defect, where it is deployed.

SUMMARY

According to one example ("Example 1"), an apparatus includes a support structure including a plurality of absorbable filaments configured to support a tissue and degrade within a defined time period; and a membrane arranged about the plurality of absorbable filaments and configured to contain fragments of the plurality of absorbable filaments in response to a fracture or degradation of a filament and promote at least one of tissue ingrowth into the membrane and tissue encapsulation of at least a portion of the membrane.

According to another example ("Example 2"), further to the apparatus of Example 1, the membrane is configured to promote healthy tissue growth and remain with the tissue after degradation of the absorbable filaments.

According to another example ("Example 3"), further to the apparatus of any one of Examples 1-2, the absorbable filaments absorbable filaments are at least one of bio-absorbable and bio-corrodible.

According to another example ("Example 4"), further to the apparatus of any one of Examples 1-3, the apparatus also includes a proximal hub arranged at a proximal end of the plurality of absorbable filaments, a distal hub arranged at a distal end of the plurality of absorbable filaments, a proximal disk configured to contact a first side of a tissue wall, and a distal disk configured to contact a second side of a tissue wall.

According to another example ("Example5"), further to the apparatus of Example 4, the apparatus also includes an elastic tensile member arranged coupled to the proximal hub and the distal hub and within the support structure, the elastic tensile member being configured to bring the proximal disk into apposition with the first side of the tissue wall and the distal disk into apposition with the second side of the tissue wall.

According to another example ("Example 6"), further to the apparatus of Example 4, the apparatus also includes a catch member arranged to, when engaged, connect the proximal hub and the distal hub within the support structure, the catch member being configured to bring the proximal disk into apposition with the first side of the tissue wall and the distal disk into apposition with the second side of the tissue wall.

According to another example ("Example 7"), further to the apparatus of Example 4, the proximal hub includes proximal end portions of the plurality of absorbable filaments and the distal hub includes distal end portions of the plurality of absorbable filaments.

According to another example ("Example 8"), further to the apparatus of Example 7, the proximal end portions of the plurality of absorbable filaments are formed together to form the proximal hub and the distal end portions of the plurality of absorbable filaments are formed together to form the distal hub.

According to another example ("Example 9"), further to the apparatus of any one of Examples 4-7, the proximal hub includes a band of material arranged about the proximal end portions of the plurality of absorbable filaments and the distal hub includes a band of material arranged about the distal end portions of the plurality of absorbable filaments.

According to another example ("Example 10"), further to the apparatus of any one of Examples 4-9, the apparatus also includes an intermediate hub including central portions of the plurality of absorbable filaments.

According to another example ("Example 11"), further to the apparatus of Example 10, the intermediate hub includes a band of material arranged about the central portions of the plurality of absorbable filaments.

According to another example ("Example 12"), further to the apparatus of any one of Examples 4-11, central portions of the plurality of absorbable filaments form a waist configured to form an open central area within the plurality of absorbable filaments.

According to another example ("Example 13"), further to the apparatus of Example 12, the waist is configured to bring the proximal disk into apposition with the first side of the tissue wall and the distal disk into apposition with the second side of the tissue wall.

According to another example ("Example 14"), further to the apparatus of any one of Examples 1-13, the membrane is configured to allow contact with blood or moisture to facilitate degradation or the plurality of absorbable filaments.

According to another example ("Example 15"), further to the apparatus of any one of Examples 1-14, the membrane includes a gap configured to allow direct tissue contact with the absorbable filaments.

According to another example ("Example 16"), further to the apparatus of any one of Examples 1-15, the membrane is non-continuous.

According to another example ("Example 17"), further to the apparatus of Example 16, the membrane includes at least two-pieces and is attached to contain the plurality of absorbable filaments.

According to another example ("Example 18"), further to the apparatus of Example 17, the membrane is configured to facilitate movement of the plurality of absorbable filaments.

According to another example ("Example 19"), further to the apparatus of any one of Examples 1-18, the plurality of absorbable filaments and the membrane are configured to facilitate crossing of atrial septum after implantation.

According to another example ("Example 20"), further to the apparatus of any one of Examples 1-19, at least one of the plurality of absorbable filaments includes a cross-section that is at least one of uneven, jagged, star-like, and polygonal.

According to one example ("Example 21"), a medical implantable occlusion device includes a braiding of at least one absorbable filament said braiding having a deployed state and an elongated state and a proximal and distal end and the braiding comprising a proximal end hub, a proximal expanded diameter portion, a center portion, a distal expanded diameter portion, and a distal hub extending along a longitudinal axis in the deployed state and configured to be stretched into a tubular formation in the elongated state; and a membrane arranged substantially about the braid and configured to contain fragments of the braid and promote at least one of tissue ingrowth into the membrane and tissue encapsulation of at least a portion of the membrane.

According to another example ("Example 22"), a method of manufacturing a medical implantable occlusion device includes any one of Examples 1-21.

According to one example ("Example 23"), a method of treating an opening in a patient includes delivering a medical device within an opening at a treatment site, the device scaffold including a plurality of absorbable filaments arranged in a support structure and configured to support a tissue and degrade within a defined time period and a membrane arranged about the plurality of absorbable filaments; degrading the plurality of filaments within the confines of the membrane; containing fragments of the plurality of absorbable filaments within the membrane in response to the fracture or degradation of the plurality of filaments; and maintaining the membrane within the opening after degradation of the plurality of filaments.

According to another example ("Example 24"), further to the method of Example 23, containing fragments of the plurality of absorbable filaments includes lessening risk of liberating particulate degradation products.

According to another example ("Example 25"), further to the method of Example 23, containing fragments of the plurality of absorbable filaments includes reducing adverse events caused by emboli in the vascular system.

According to another example ("Example 26"), an apparatus includes an absorbable support structure configured to support a tissue and degrade within a defined time period; and a membrane arranged about the absorbable structure and configured to contain fragments of the absorbable structure in response to a fracture or degradation of a portion of the absorbable structure and promote at least one of tissue ingrowth into the membrane and tissue encapsulation of at least a portion of the membrane.

According to another example ("Example 27"), further to the apparatus of Example 26, the absorbable structure is formed from a cut-tube, cut-sheet, filaments, an injection molding, or additive printing.

According to another example ("Example 28"), further to the apparatus of Example 26, the absorbable structure and the membrane are configured to implant within vasculature or appendage of a patient.

According to another example ("Example 29"), further to the apparatus of Example 26, the apparatus also includes a plug arranged at one end of the absorbable structure.

According to another example ("Example 30"), further to the apparatus of Example 26, the membrane is at least partially absorbable and configured to facilitate healthy tissue ingrowth The foregoing Examples are just that, and should not be read to limit or otherwise narrow the scope of any of the inventive concepts otherwise provided by the instant disclosure. While multiple examples are disclosed, still other embodiments will become apparent to those skilled in the art from the following detailed description, which shows and describes illustrative examples. Accordingly, the drawings and detailed description are to be regarded as illustrative in nature rather than restrictive in nature.

BRIEF DESCRIPTION OF THE DRAWINGS

The accompanying drawings are included to provide a further understanding of the disclosure and are incorporated in and constitute a part of this specification, illustrate embodiments, and together with the description serve to explain the principles of the disclosure.

DETAILED DESCRIPTION

Definitions and Terminology

Figure 1:
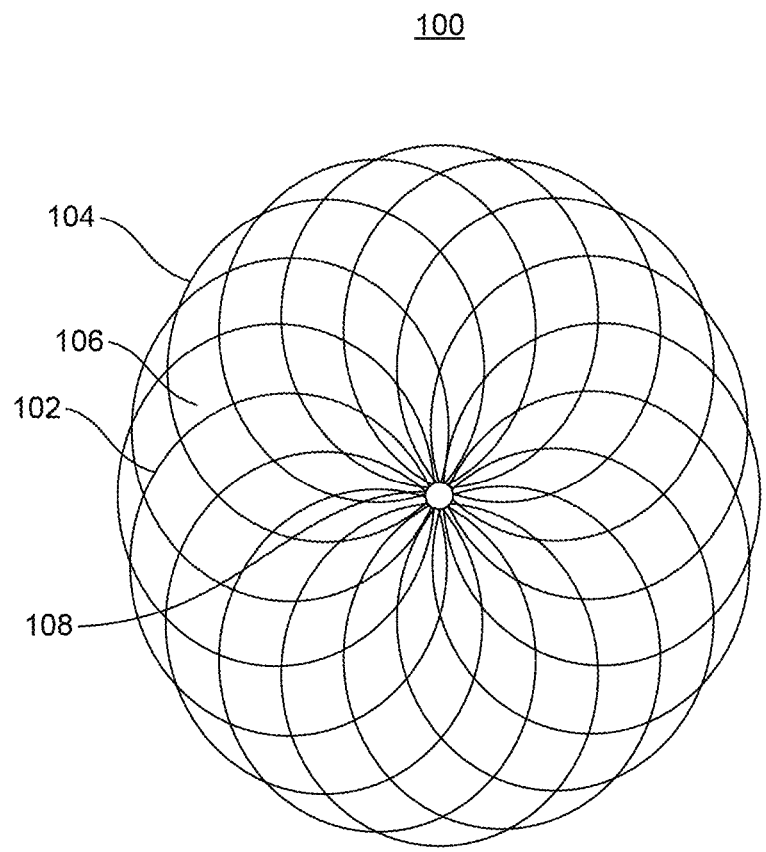
FIG. 1 is an end view illustration of an example occluder, in accordance with an embodiment.

Persons skilled in the art will readily appreciate that various aspects of the present disclosure can be realized by any number of methods and apparatus configured to perform the intended functions. It should also be noted that the accompanying drawing figures referred to herein are not necessarily drawn to scale, but may be exaggerated to illustrate various aspects of the present disclosure, and in that regard, the drawing figures should not be construed as limiting.

This disclosure is not meant to be read in a restrictive manner. For example, the terminology used in the application should be read broadly in the context of the meaning those in the field would attribute such terminology.

With respect terminology of inexactitude, the terms "about" and "approximately" may be used, interchangeably, to refer to a measurement that includes the stated measurement and that also includes any measurements that are reasonably close to the stated measurement. Measurements that are reasonably close to the stated measurement deviate from the stated measurement by a reasonably small amount as understood and readily ascertained by individuals having ordinary skill in the relevant arts. Such deviations may be attributable to measurement error or minor adjustments made to optimize performance, for example. In the event it is determined that individuals having ordinary skill in the relevant arts would not readily ascertain values for such reasonably small differences, the terms "about" and "approximately" can be understood to mean plus or minus 10% of the stated value.

Description of Various Embodiments

Various aspects of the present disclosure are directed toward medical devices having one or more absorbable filaments (e.g., bio-degradable or bio-corrodible) that are arranged to form the medical device. The absorbable filaments may be bio-corrodible, bio-degradable, or both (e.g., a combination of) bio-corrodible and bio-degradable. The absorbable filaments (which may be struts, a fiber, braided, woven fibers, combined fibers, or other structural elements) may degrade or dissolve through one or more varieties of chemical and/or biological based mechanisms that result in a tissue response suitable for the intended implant application. A membrane may be arranged with or attached to at least a portion of the one or more filaments. The membrane may be configured to structurally enhance and/or maintain integrity of the filaments during degradation or fracture. The medical devices may include, for example, a stent or stent-graft, occluders for placement within and closure of a tissue opening (e.g., Patent foramen ovale (PFO) or atrial septal defects (ASD)), vascular closure devices, or other similar devices. In certain instances, the absorbable filaments are configured to structurally enhance or support the space (opening) into which the medical device is implanted. In certain instances, the bio-degradable or bio-corrodible filaments degrade while the membrane facilitates healthy tissue ingrowth or regrowth such that the structure provided by the bio-degradable or bio-corrodible filaments may become unnecessary.

Absorbable herein refers to materials capable of being absorbed by the body, be it directly through dissolution or indirectly through degradation of the implant into smaller components that are then absorbed. The term absorbable also is used herein cover a variety of alternative terms to that have been historically utilized interchangeably both within and across surgical disciplines (but intermittently with inferred differentiation), Those terms include, for example, absorbable and its derivatives, degradable and its derivatives, biodegradable and its derivatives, resorbable and its derivatives, bioresorbable and its derivatives, and biocorrodible and its derivatives. The term absorbable, as used herein, may encompass multiple degradation mechanisms, which include, but are not limited to, corrosion and ester hydrolysis. Further reference may be made to Appendix X4 of ASTM F2902-16 for additional absorbable-related nomenclature.

In addition, filaments, as discussed herein, may include a monofilament, which can also be described as a single fiber, strand, wire, rod, bead, or other non-rigid elongated substantially cylindrical embodiment with a longitudinal dimension that exceeds that of its cross section by greater than 100×. The monofilament may optionally possess one or more overlay coatings or other surface modifications to provide features that are not inherent to its underlying base structure. Further, the devices described herein, although described as including and being formed of a filament or filaments, may be formed by other means such as a cut-tube (e.g., laser scission and subsequent expansion and shape setting of polymeric or metal tubing) as described with reference to FIG. 9.

Figure 7:
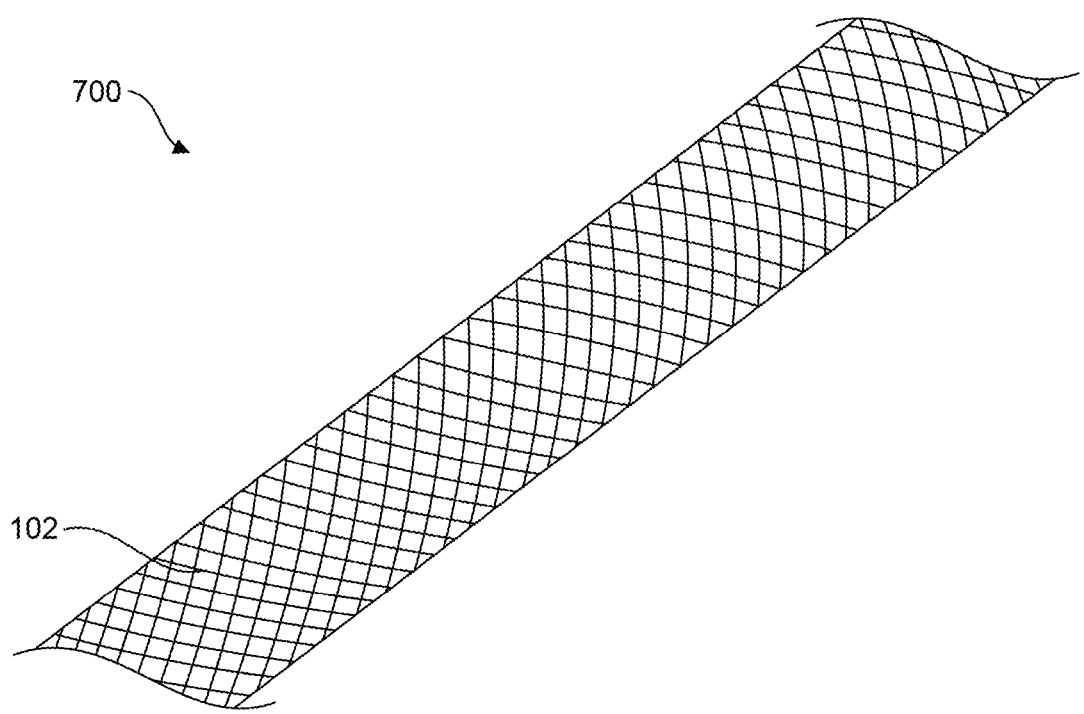
FIG. 7 is an illustration of a tubular arrangement may then be shape set into a medical device, in accordance with an embodiment.

FIG. 1 is an end view illustration of an example occluder 100, in accordance with an embodiment. The occluder 100 may be formed of at least one absorbable filament 102. The at least one absorbable filament 102 may be braided into a frame that forms the occluder 100. In certain instances, the at least one absorbable filament 102 may include a substantially circular perimeter 104. The at least one absorbable filament 102 may have an overlapping arrangement (e.g., formed via braiding, weaving, winding, or other processing techniques). In certain instances, the absorbable filament(s) 102 may overlap one another in a balanced tubular arrangement (as shown in FIG. 7). The tubular arrangement may then be shape set into a desired shape such as an occluder. The shape set process may also occur using a solvent, and may also occur through other means such as polymeric imbibing through an appropriate fluid or heat setting. In addition, the at least one absorbable filament 102 may create open cells 106 between overlapping filaments 102 within the substantially circular perimeter 104.

In certain instances, the open cells 106 within the substantially circular perimeter 104 are formed by weaving of the at least one absorbable filament 102. In addition, the at least one absorbable filament 102 may be interwoven or braided into a tubular structural and formed into the occluder 100 having the substantially circular perimeter 104. The at least one absorbable filament 102 may be formed into a device that includes one or more disks, such as two disks as shown (e.g., a proximal and distal disks or expanded diameter portions). The end view shown in FIG. 1 shows a single disk.

As shown in FIG. 1, the at least one absorbable filament 102 may converge at ends of the occluder 100 to form a hub 108. The hub 108 may include an additional band, eyelet, or material that crimps or holds the end portions of the at least one absorbable filament 102 together. In certain instances, the end portions of the at least one absorbable filament 102 may be bonded, melted, or otherwise formed together to form the hub 108. As explained in further detail below, a membrane may be arranged substantially about the braid and configured to contain or restrain fragments of the braid and promote tissue attachment and/or tissue ingrowth.

Figure 2:
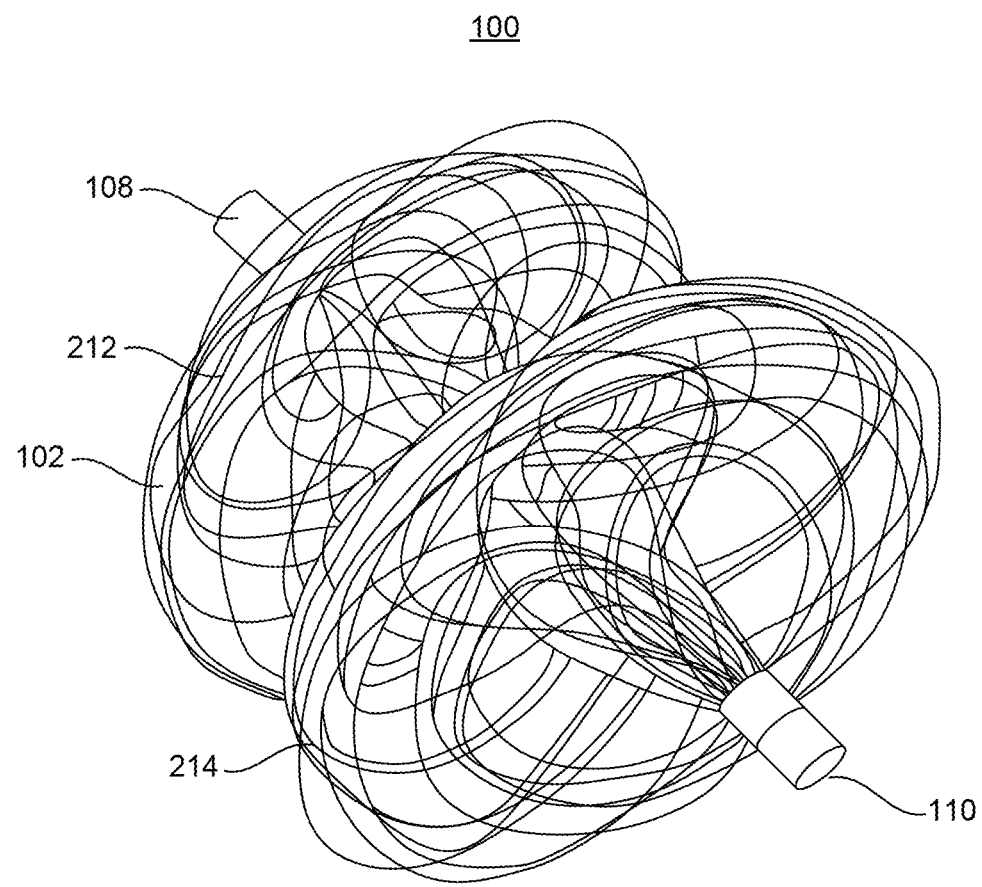
FIG. 2 is a perspective view illustration of an example occluder, in accordance with an embodiment.

FIG. 2 is a perspective view illustration of an example occluder 100, in accordance with an embodiment. The occluder 100 may include a plurality of absorbable filaments 102 arranged in a support structure. The plurality of absorbable filaments 102 are configured to support a tissue and degrade within a defined time period. As shown, the plurality of absorbable filaments 102 are interwoven to form the support structure.

As shown in FIG. 2, the occluder 100 includes proximal hub 108 arranged at a proximal end of the plurality of absorbable filaments 102 and a distal hub 110 arranged at a distal end of the plurality of absorbable filaments 102. In certain instances, the proximal hub 108 includes proximal end portions of the plurality of absorbable filaments 102 and the distal hub 110 includes distal end portions of the plurality of absorbable filaments 102. The proximal end portions of the plurality of absorbable filaments 102 and the distal end portions of the plurality of absorbable filaments 102 may be separately molded, woven, or arranged together and held in place with the proximal hub 108 and the distal hub 110 being bands of material arranged about the proximal end portions of the plurality of absorbable filaments 102.

In addition, the occluder can include a proximal disk 212 configured to contact a first side of a tissue wall and a distal disk 214 configured to contact a second side of a tissue wall. The proximal disk 212 and the distal disk 214 are formed by braiding of the plurality of absorbable filaments 102. The plurality of absorbable filaments 102 may be interwoven or braided together in a structure and set into shape, which includes the proximal disk 212, the distal disk 214, proximal hub 108, and distal hub 110.

In certain instances and as discussed in further detail below with reference to FIG. 6, the occluder 100 of FIG. 2 may include a membrane arranged about the plurality of absorbable filaments 102. The membrane (not shown) and configured to contain or restrain fragments of the plurality of absorbable filaments 102 in response to the fracture or degradation of the filament and promote tissue ingrowth into the membrane. In addition and as discussed in detail below, the absorbable filaments 102 prevent embolization of device through the opening into which it is implanted (e.g., PFO) and are configured to apply appositional forces against the septum such that the membrane may facilitate tissue attachment, tissue ingrowth, and/or tissue encapsulation to close the opening.

Figure 3:
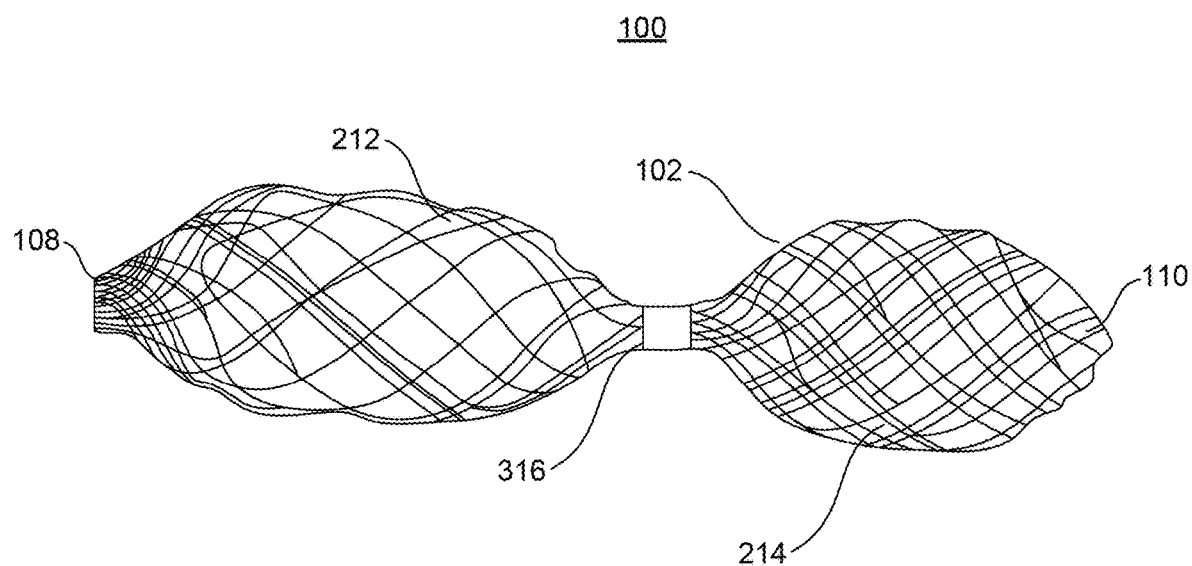
FIG. 3 is a side view of an example occluder in an elongated configuration, in accordance with an embodiment.

FIG. 3 is a side view of an example occluder 100 in an elongated configuration, in accordance with an embodiment. The occluder 100 may include a plurality of absorbable filaments 102 includes a braiding that has a proximal hub 108, a proximal expanded diameter portion (e.g., a proximal disk) 212, an intermediate or center hub 316, a distal expanded diameter portion (e.g., a distal disk) 214, and a distal hub 110. Each of the elements extend along a longitudinal axis (between the hubs 108, 110) in the deployed state and the braiding formed by the plurality of absorbable filaments 102 is configured to be stretched into a tubular formation in the loaded state (or elongated configuration) as shown in FIG. 3. The braided plurality of absorbable filaments 102 may retract or are retracted to form disks that conform to patient anatomy. In certain instances, the braided plurality of absorbable filaments 102 are configured to maintain contact with tissue in response to physiological movements of a patient's heart.

In certain instances, proximal end portions of the plurality of absorbable filaments 102 are formed together to form the proximal hub 108 and distal end portions of the plurality of absorbable filaments 102 are formed together to form the distal hub 110. In certain instances, the respective end portions may be bonded, melted, or otherwise formed together to for the hubs 108, 110. As shown in FIG. 3, the occluder also may have an intermediate hub 316 that includes central portions of the plurality of absorbable filaments 102. The intermediate hub 316 may include a band of material arranged about the central portions of the plurality of absorbable filaments 102, or as shown in FIG. 3, the central portions of the plurality of absorbable filaments 102 may be bonded, melted, or otherwise formed together to form the intermediate hub 316. In certain instances, the hubs 108, 110 (and/or hub 316) may be formed of or include a radiopaque material (e.g., gold, tantalum, platinum iridium, tungsten) to facilitate deployment of the device 100.

In certain instances, the device 100 (and other devices discussed herein) may be formed of absorbable and non-absorbable filaments 102. In these instances, 102 of the scaffold of the device 100 formed by non-absorbable filaments 100 may remain in situ. In instances where the device 100 (and other devices discussed herein) include absorbable and non-absorbable filaments 102, the structural integrity of tissue may be supported in addition to having the membrane 520 remain in vivo by non-absorbable filaments 102 remaining in vivo.

Figure 4:
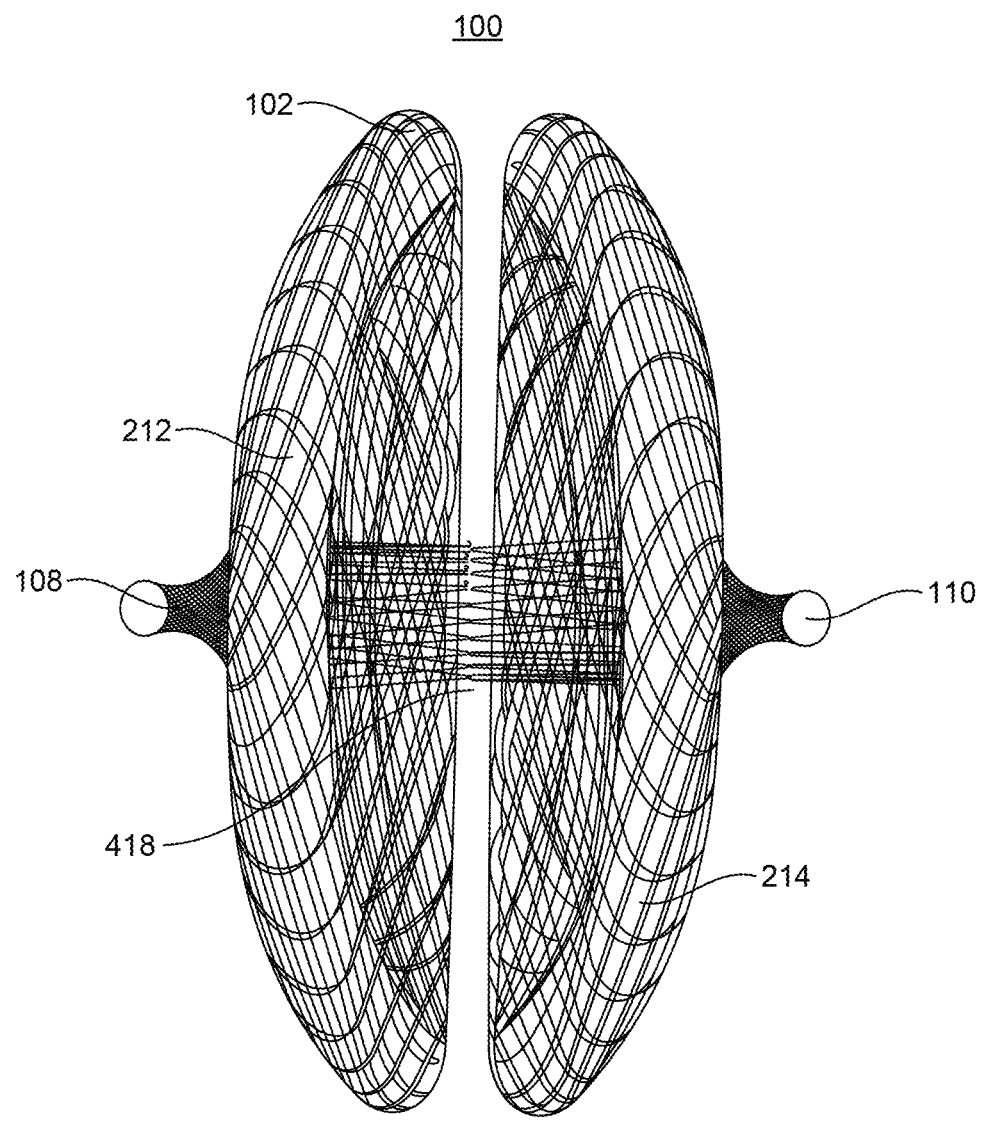
FIG. 4 is a side view of another example occluder, in accordance with an embodiment.

FIG. 4 is a side view of another example occluder 100, in accordance with an embodiment. The occluder 100 may include a plurality of absorbable filaments 102 arranged in a support structure. The plurality of absorbable filaments 102 are configured to support a tissue and degrade within a defined time period. As shown, the plurality of absorbable filaments 102 are interwoven to form the support structure.

The occluder 100 includes proximal hub 108 arranged at a proximal end of the plurality of absorbable filaments 102 and a distal hub 110 arranged at a distal end of the plurality of absorbable filaments 102. In certain instances, the proximal end 108 includes proximal end portions of the plurality of absorbable filaments 102 and the distal hub 110 includes distal end portions of the plurality of absorbable filaments 102. The proximal end portions of the plurality of absorbable filaments 102 and the distal end portions of the plurality of absorbable filaments 102 may be woven such that the end portions or hubs 108, 110 are planar with or do not substantially protrude beyond ends of the device (e.g., a closed-loop braided disc).

Ends of the occluder 100 can include a proximal disk 212 configured to contact a first side of a tissue wall and a distal disk 214 configured to contact a second side of a tissue wall. The proximal disk 212 and the distal disk 214 are formed by braiding of the plurality of absorbable filaments 102. The plurality of absorbable filaments 102 may be interwoven or braided together in a structure and set into shape, which includes the proximal disk 212, the distal disk 214, proximal hub 108, and distal hub 110. In an elongated configuration, as shown in FIG. 4, the proximal disk 212 and the distal disk 214 may be bulbous. In a deployed configuration, the proximal disk 212 and the distal disk 214 (as well as the hubs 108, 110) with end sides of the proximal disk 212 and the distal disk 214 being substantially flat and include a thickness in the range of approximately 0.5 mm to 2 mm or twice the filament 102 diameter. Inner portions of the proximal disk 212 and the distal disk 214 may taper into a waist 418.

The waist 418 may be formed of central portions of the plurality of absorbable filaments 102. In addition, the waist 418 may be configured to form an open central area within the plurality of absorbable filaments 102 in each of the deployed and elongated configuration. The waist 418 may be configured to bring the proximal disk 212 into apposition with a fist side of the tissue wall and the distal disk 214 into apposition with the second side of the tissue wall.

Figure 5:
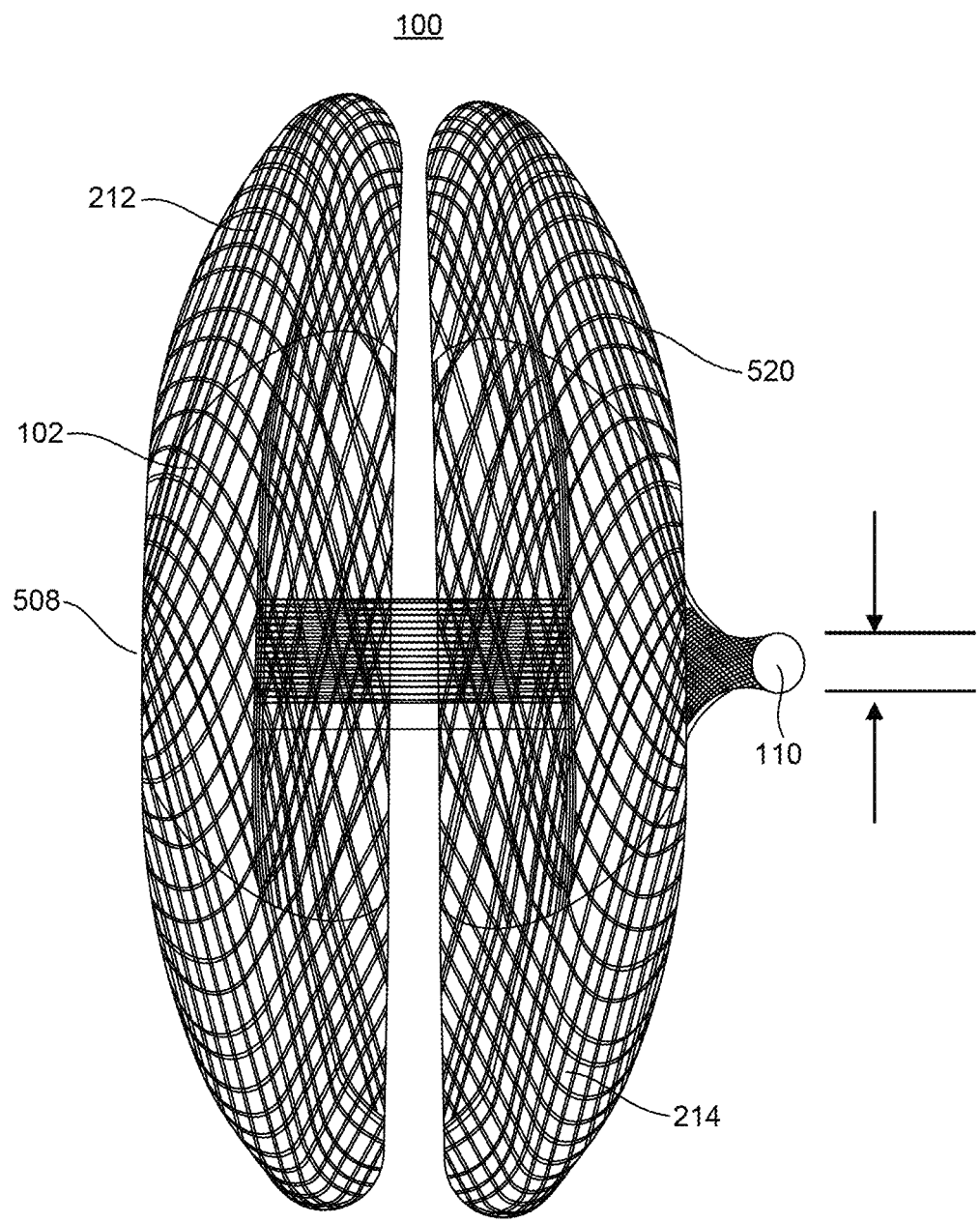
FIG. 5 is a partial cutaway side view of another example occluder in a deployed configuration, in accordance with an embodiment.

FIG. 5 is a partial cutaway side view of another example occluder 100 in a deployed configuration, in accordance with an embodiment. The occluder 100 may include a plurality of absorbable filaments 102 arranged in a support structure. The plurality of absorbable filaments 102 are configured to support a tissue and degrade within a defined time period and may be interwoven to form the support structure.

The occluder 100 includes a distal hub 110 arranged at a distal end of the plurality of absorbable filaments 102. As discussed in detail above, the distal hub 110 includes distal end portions of the plurality of absorbable filaments 102. As shown in FIG. 5, a proximal end 508 of the occluder 100 is an integral portion of a proximal disk 212. The proximal end portions of the plurality of absorbable filaments 102 are woven such that the end portions or hubs 108, 110 are planar with or do not substantially protrude beyond ends of the occluder 100. In certain instances, the proximal disk 212 may be a closed loop braided disk such that there are no producing features. The distal disk 214 may be similarly formed such that the distal disk 214 does not include the distal hub 110. In this instance, the proximal and distal designations are not indicative of the orientation of implantation within the body. For example, the proximal end 508 of being an integral portion of the proximal disk 212 may be implanted in the left atrial to minimize thrombus formation.

Ends of the occluder 100 can include a proximal disk 212 configured to contact a first side of a tissue wall and a distal disk 214 configured to contact a second side of a tissue wall. The proximal disk 212 and the distal disk 214 are formed by braiding of the plurality of absorbable filaments 102. The plurality of absorbable filaments 102 may be interwoven or braided together in a structure and set into shape, which includes the proximal disk 212, the distal disk 214, proximal hub 108, and distal hub 110. The proximal disk 212 and the distal disk 214 may be formed into different shapes as shown in FIG. 5. In addition, inner portions of the proximal disk 212 and the distal disk 214 may taper into a waist 418.

The waist 418 may be formed of central portions of the plurality of absorbable filaments 102. In addition, the waist 418 may be configured to form an open central area within the plurality of absorbable filaments 102 in each of the deployed and elongated configuration. The waist 418 may be configured to bring the proximal disk 212 into apposition with a first side of the tissue wall and the distal disk 214 into apposition with the second side of the tissue wall.

As shown, the absorbable filaments 102 may be braided to form a scaffold and the absorbable filaments 102 are configured to degrade over time. In certain instances, braiding provides a stent structure that is flexible and conformable in nature allowing the device 100 to conform naturally to the tissue and anatomy. The braid construct is also balanced with an even number helically wound and interwoven filaments 102 in multiple directions. The balancing of the braid may allow for device 100 to naturally expand into its intended shape by lessening internal bound twisting or bending forces.

In addition, a membrane 520 may be attached (e.g., using medical adhesive) to a perimeter of the absorbable filaments 102. The medical adhesive may also be absorbable. In certain instances, the membrane 520 may be porous such that fluid or moisture exchange occurs through the pores of the membrane 520 allowing degradation of the absorbable filaments 102. In other instances, the absorbable filaments 102 may naturally degrade within a non-porous membrane.

In certain instances, the membrane 520 may be configured to facilitate healthy tissue ingrowth or regrowth. This tissue attachment to the membrane 520 ensures fixation within the anatomy such that the structure provided by the absorbable filaments 102 become unnecessary. The membrane 520 may possess surface structure that may stabilize the device 100 such that fragments of the absorbable filaments 102 are restricted from movement from the treatment site. In certain instances, the membrane 520 may facilitate tissue ingrowth or encapsulation or attachment of the structure of the absorbable filaments 102.

In addition, the membrane 520 may fully encapsulate and provide a porous jacketed material around the filaments 102. The membrane 520 surrounding the filaments 102 may include a tensile strength and toughness to provide ongoing structural integrity while allowing degradation and fluid or moisture exchange to occur thru the open porosity of the membrane 520 to the filaments 102. In certain instances, the filaments 102, acting as a temporary scaffold, are configured to provide enough outward force and/or pressure to allow the membrane 520 to buttress up against the tissue to maintain contact during an initial time period (e.g., 30-60 days) in vivo and maintain a scaffold structure for the tissue after the filaments 102 degrade. The membrane 520 may be arranged about the filaments 102 and configured to contain or restrain fragments of the filaments 102 and maintain structure of the device 100 in response to the fracture or degradation of the filaments 102. In certain instances, the filaments 102 degrade within the confines of the membrane 520.

Containing or restraining fragments of the plurality of absorbable filaments 102 lessens risk of liberating particulate degradation products as compared to a non-covered absorbable filament. In addition, containing fragments of the absorbable filaments 102 may reduce the chances of migration and potential adverse events caused by thrombus formation or the generation of emboli in the vascular system.

As noted above, the membrane 520 may be porous. The porosity of the membrane 520 may control or impact the rate at which the filaments 102 degrade. The filaments 102 and the membrane 520 may be implanted into a patient to enhance or repair unhealthy or poorly formed tissue. As noted above, the device 100 may be implanted within a PFO or ASD opening. The device 100 may seal the opening or otherwise prevent or reduce shunting across the septal wall. Micro-vascularized tissue ingrowth into and through or over the membrane 520 may facilitate healthier overall tissue growth and restore of the structural integrity of tissue to seal the opening. In certain instances, the filaments 102 being degradable allows for closure of the opening with the generally more bio-compatible membrane 520 remaining in place as opposed to a metallic or semi-metallic filament.

In certain instances, one or more of the filaments 102 may be coated or imbibed with a therapeutic agent. The membrane 520 will have an engineered porosity that controls therapeutic drug release, contains degradation products until their physical or chemical dimensions are reduced to a size that allows them to pass through the pores and/or the resulting membrane/tissue composite. In certain instances, the membrane 520 may be configured to maintain fragments from moving away from the treatment site prior to being reduced to sizes sufficiently small that can they can be benignly absorbed by the patient.

In addition, one or more of the filaments 102 may be an absorbable metal (such as magnesium) and the membrane 520 may be a non-degradable polymer (such as ePTFE). This device may also provide radiopacity and initial strength due to the metal framework of the one or more of the filaments 102 if the one or more of the filaments 102 are formed of a metallic degradable material or the device may include radiopacity if the membrane 520 is imbibed with radiopaque material.

In certain instances, the membrane 520 may be absorbable or partially absorbable. The membrane 520, if absorbable, may have an equal or shorter longevity than the absorbable filaments 102. The membrane 520, in these instances, may enhance/augment tissue coverage over the underlying absorbable filaments 102. The membrane 520, in these instances, may effectively restrain or contain migration of fragments or particulates that may emanate from the absorbable filaments 102 during degradation or fracture of the absorbable filaments 102. Similar to non-absorbable membranes, the membrane 520 being degradable may allow for tissue attachment and/or ingrowth that stabilizes the overlying tissue so it can contain or substantially restrain migration of fragments and particulate matter emanating from degrading filaments. A porous absorbable membrane 520 that may retain strength and/or ability to provide stable and reinforced overlying tissue for a duration longer than that of the degrading filaments 102 is preferred. The membrane 520 may include portions that are absorbable and portions that are non-absorbable (e.g., a partially absorbable membrane 520).

Figure 6:
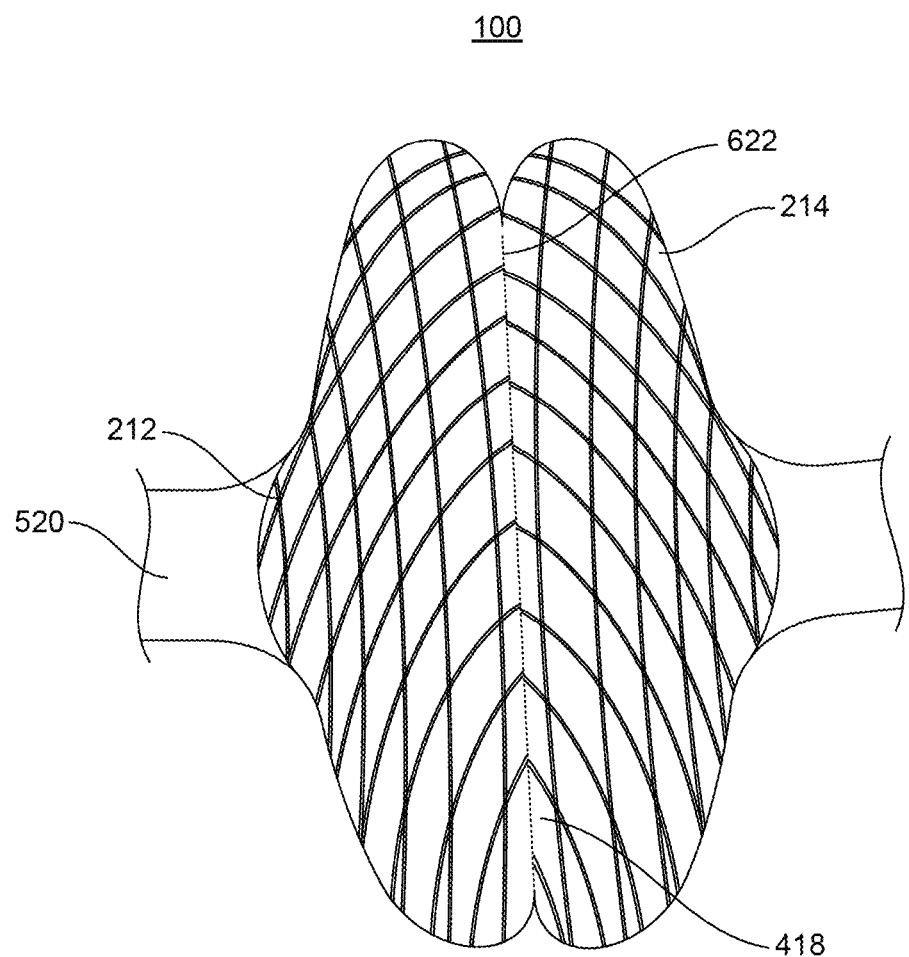
FIG. 6 is a side view of another example occluder with a membrane, in accordance with an embodiment.

FIG. 6 is a side view of another example occluder 100 with a membrane 520, in accordance with an embodiment. The membrane 520 may be arranged about a plurality of absorbable filaments (as discussed in detail above) and configured to contain fragments of the plurality of absorbable filaments in response to the fracture or degradation of the filament and promote tissue ingrowth into the membrane. In certain instances, the membrane 520 is configured to promote healthy tissue growth and remain with the tissue after degradation of the absorbable filaments. The absorbable filaments 102 are configured to structurally enhance or hold-open the space into which the occluder is implanted. The absorbable filaments 102 prevent embolization of the device through the opening into which it is implanted (e.g., PFO) and are configured to apply appositional forces against the septum such that the membrane 520 may facilitate tissue ingrowth close to the opening. During degradation of the bio-degradable or bio-corrodible filaments, the membrane 520 facilitates healthy tissue ingrowth or regrowth such that the structure provided by the bio-degradable or bio-corrodible filaments may become unnecessary. The membrane 520 maintains within the patient and provides structure without a metallic structure remaining as would occur with a non-degradable stent.

In certain instances, the membrane 520 is configured to allow contact with blood without fragments of pieces of the filaments 102 escaping the membrane 520. The membrane 520 may allow fluid or moisture through without allowing fragments or pieces of the filaments to escape (which may lead to emboli formation).

In certain instances, the membrane 520 includes a gap 622 and is configured to allow direct tissue contact and encapsulation of the absorbable filaments 102. The gap 622 may face a septal wall to facilitate tissue attachment or ingrowth for further stabilization of the occluder 100. In addition, the membrane 520 may be non-continuous. Further, the membrane 520 may also be formed in two-pieces (separated by the gap 622) and attached to the plurality of filaments. In these instances, the membrane 520 may be configured to facilitate movement of the plurality of absorbable filaments 102. The membrane 520 may be attached to the filaments at one or more locations.

The plurality of absorbable filaments 102 and the membrane 520 may be configured to facilitate crossing of a (atrial) septum after implantation. Degradation of the filaments may leave an access point in tissue such that the (atrial) septum may be re-crossed after implantation for other procedures.

In certain instances, the filaments absorb or degrade within a year and also preserve, when implanted in an atrium septum, access to the left atrium for future trans-septal procedures. The absorbable frame construct can help eliminate uncertainty caused by metal frame fractures. In addition, an internal film patch (not shown) may be used inside braided disks to facilitate creation of a closure seal.

FIG. 7 is an illustration of a tubular arrangement 700 may then be shape set into a medical device, in accordance with an embodiment. The tubular arrangement 700 may include filaments 102 that are braided together. The filaments 102 may be absorbable filaments, as discussed in detail above, or the filaments 102 may be formed of a non-absorbable polymer (e.g., polyester, nylon, Polyether ether ketone (PEEK))

Figure 8:
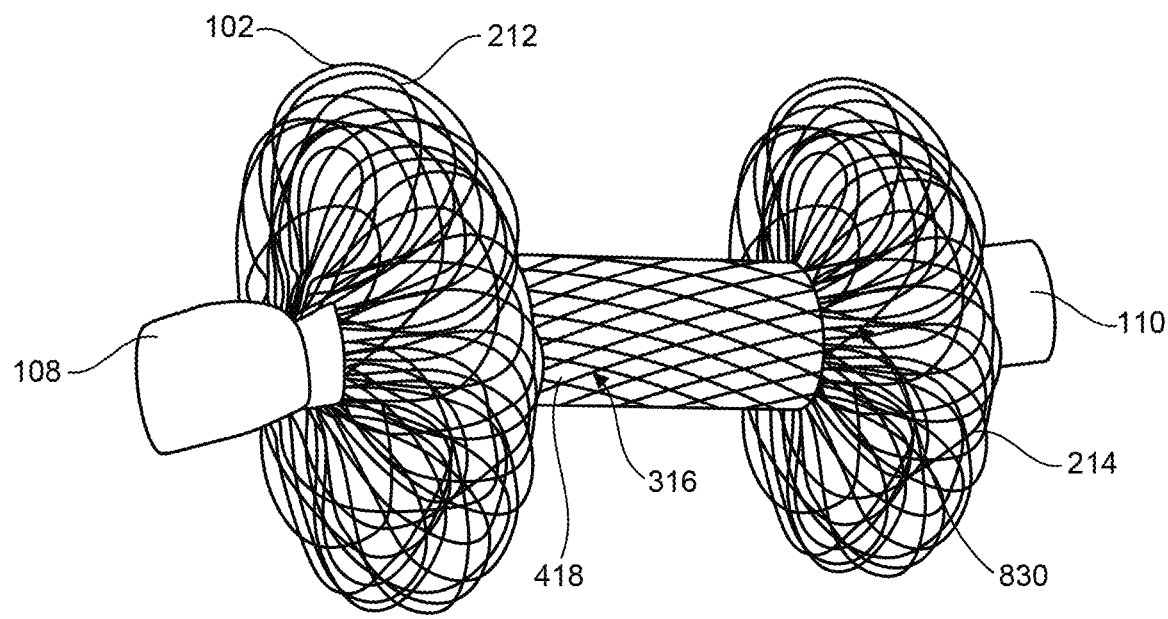
FIG. 8 is an example medical device formed of the tubular arrangement shown in FIG. 7, in accordance with an embodiment.

The filaments 102, whether absorbable or non-absorbable, may be braided to form the tubular arrangement 700. The filaments 102 may be woven helically together into the tubular arrangement 700. In certain instances, braiding provides a structure that is flexible and conformable in nature allowing devices formed from the tubular arrangement 700 to conform naturally to the tissue and anatomy. The braid construct is also balanced with an even number helically wound and interwoven filaments 102 in multiple directions. The balancing of the braid may allow for a device formed from the tubular arrangement 700 to naturally expand into its intended shape by lessening internal bound twisting or bending forces. The tubular arrangement may then be shape set into a desired shape such as an occluder, for example, as shown in FIG. 8. The tubular arrangement 700 can also be molded into the devices shown in FIGS. 1-6.

FIG. 8 is an example medical device 100 formed of the tubular arrangement 700 shown in FIG. 7, in accordance with an embodiment. The medical device 100 shown in FIG. 8 may be formed by molding the tubular arrangement 700 into the shape shown, and shape set.

The medical device 100 may be similarly constructed as described in detail above. For example, the medical device 100 may include filaments 102 that are braided together. The filaments 102 may be absorbable filaments, as discussed in detail above, or the filaments 102 may be formed of a non-absorbable polymer. As discussed in detail above in instances where the filaments 102 are absorbable filaments 102, the absorbable filaments 102 are configured to support a tissue and degrade within a defined time period and may be interwoven to form a support structure.

The device 100 includes a distal hub 110 arranged at a distal end of the filaments 102. As discussed in detail above, the distal hub 110 includes distal end portions of the filaments 102. In addition, the proximal hub 108 includes proximal end portions of the filaments 102. In certain instances, the proximal end portions or the distal end portions of the filaments 102 are woven such that the end portions or hubs 108, 110 are planar with or do not substantially protrude beyond ends of the device 100. In certain instances, the proximal disk 212 or the distal disk 214 may be a closed loop braided disk such that there are no protruding features.

Ends of the occluder 100 can include a proximal disk 212 configured to contact a first side of a tissue wall and a distal disk 214 configured to contact a second side of a tissue wall. The proximal disk 212 and the distal disk 214 are formed by braiding of the filaments 102. The filaments 102 may be interwoven or braided together in a structure and set into shape, which includes the proximal disk 212, the distal disk 214, proximal hub 108, and distal hub 110. In addition, inner portions of the proximal disk 212 and the distal disk 214 may taper into a waist 418.

The waist 418 may be formed of central portions of the filaments 102. In addition, the waist 418 may be configured to form an open central area within the filaments 102 in each of a deployed and elongated configuration. The waist 418 may be configured to bring the proximal disk 212 into apposition with a fist side of the tissue wall and the distal disk 214 into apposition with the second side of the tissue wall.

In certain instances, the device 100 may include an elastic tensile member 830 arranged between the hubs 108, 110 and within the waist 418. In certain instances, the elastic tensile member 830 may be configured to snap the device 100 together when stretched or elongated or otherwise return the distal and proximal hubs 108, 110 together. The elastic tensile member 830 may facilitate the device 100 maintaining the intended deployed configuration shown in FIG. 8. The elastic tensile member 830 may be adhered or coupled to the hubs 108, 110. In addition, the elastic tensile member 830 may be stretched and held at an elastic limit.

The elastic tensile member 830 may be configured to create an apposition force between the disks 212, 214 of the device 100 when the device 100 is deployed. The apposition force may be increased relative to a device 100 that does not include the elastic tensile member 830. The elastic tensile member 830 may be under tension when the device 100 is deployed. As the device 100 is elongated, tension in the elastic tensile member 830 increases but stays below a tensile limit of the elastic tensile member 830. When the device 100 is released from its elongated state, tensile force in the elastic tensile member 830 acts to pull the disks 212, 214 together with additional force.

In certain instances, the waist 418 may include an intermediate hub 316 that surrounds the central portions of the filaments 102. The intermediate hub 316 may include a band of material (e.g., ePTFE) arranged about the central portions of the filaments 102. The band of material about the intermediate hub 316 may maintain a diameter of the waist 418 during stretching of the device 100 and the elastic tensile member 830.

In addition, a membrane (not shown) may be attached (e.g., using medical adhesive) to a perimeter of the filaments 102. In certain instances, the membrane may be porous such that fluid or moisture exchange occurs through the pores of the membrane allowing degradation of the filaments 102. In certain instances, the membrane 520 may be configured facilitate healthy tissue encapsulation of the membrane 520, tissue ingrowth into the membrane 520, and/or regrowth of tissue. The elastic tensile member 830 may also be formed of an absorbable material such that only the membrane is left behind as discussed in detail above.

Figure 9:
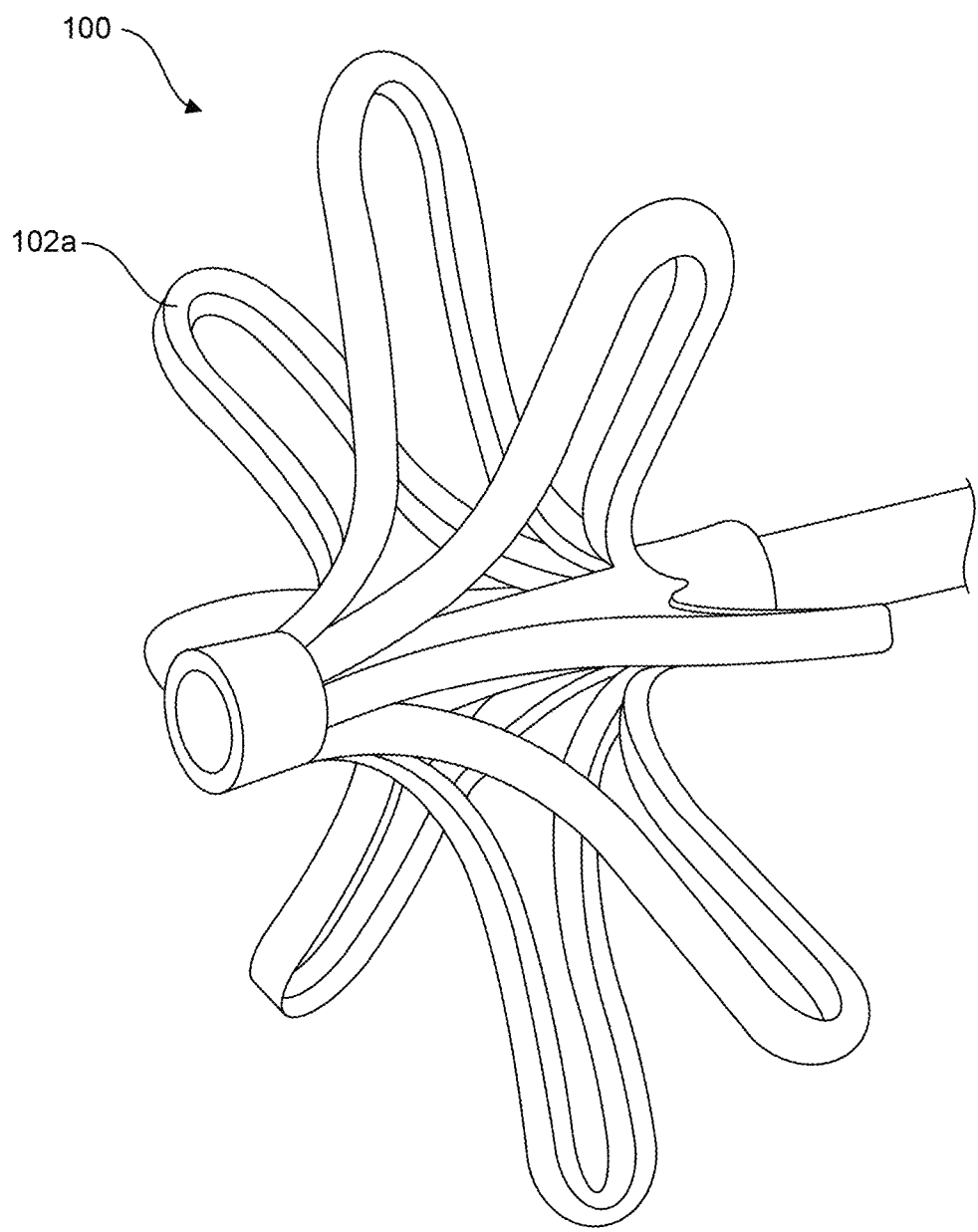
FIG. 9 is an expanded medical device formed of a cut-tube, in accordance with an embodiment.

FIG. 9 is an expanded medical device 100 formed of a cut-tube, in accordance with an embodiment. A tube or structure of material may be laser cut or incised to form the medical device 100 shown in FIG. 9. In certain instances and as shown in FIG. 9, the medical device 100 may include frame elements 102a that fan outwardly in a deployed configuration. This medical device 100 may include disks as described in detail above.

Figure 10:
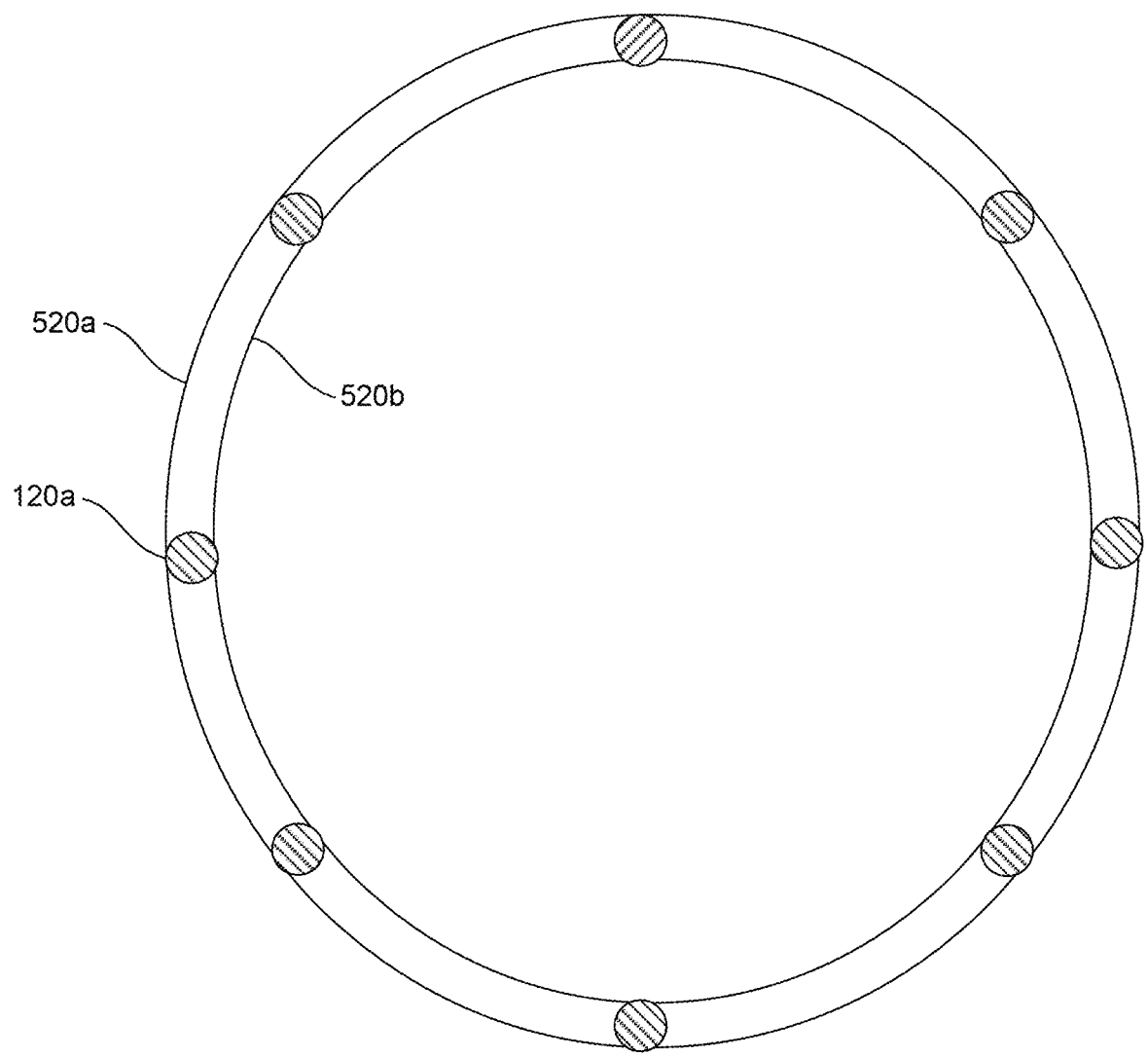
FIG. 10 is a cross-sectional view of an example stent, in accordance with an embodiment.

FIG. 10 is a cross-sectional view of an example stent, in accordance with an embodiment. The stent may include frame elements 102a (which may be filaments 102 or cut-tube elements) that may be formed of filaments or may be formed of a cut-tube. For example, the stent may be tubular as shown in FIG. 7 or include a helical pattern of struts or discrete stent rings. The stent, or other medical devices discussed herein, may be arranged between layers of membrane 520a, 520b. The layers of membrane 520a, 520b (properties of which are discussed in detail above) may sandwich the frame elements 102a. The frame elements 102a may be absorbable.

Figure 11:
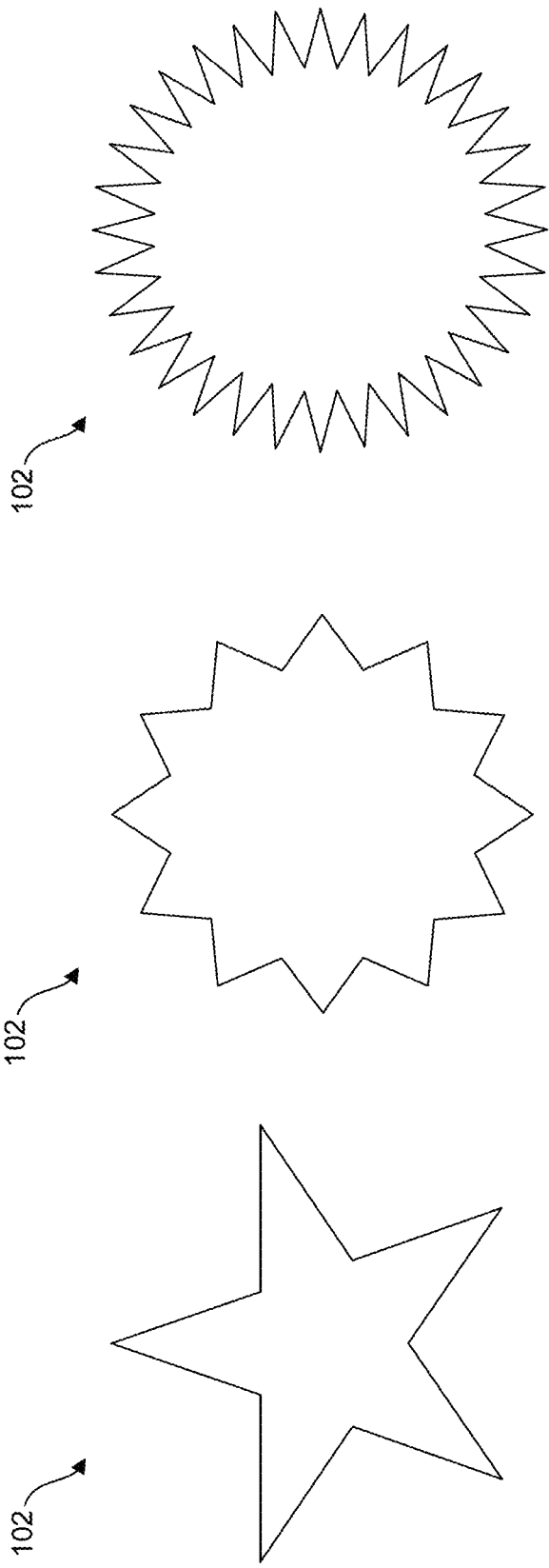
FIGS. 11A-C are illustrations of example filament cross-sections, in accordance with an embodiment.

FIGS. 11A-C are illustrations of example filament 102 cross-sections, in accordance with an embodiment. As shown and discussed in detail above, a filament 102 may include a substantially circular cross-section. In other instances and as shown in FIGS. 11A-C, the filament 102 may include a cross-section that is not substantially circular in cross-section.

The filament 102, for example, may be formed or drawn to include a star-like cross-section. The star-like or polygonal cross-section of the filament 102, as shown in FIGS. 11A-C, may increase surface area of the filament 102 as compared to a filament 102 having a substantially circular cross-section. As a result, the degradation profile of the filament 102 formed from a polymer susceptible to enzymatic degradation at its surface may be tailored based on the cross-section of the filament 102. The filament 102, for example, may have a faster degradation profile or rate with a great surface area. Conversely, in bulk hydrolysable polymers the higher cross-sectional surface-to-volume ratio of the star or polygon shapes may, through effective reduction of the core-to-outer-surface distance of the filament 102, comparatively slow hydrolytic degradation by reducing the risk of acid catalysis presented by concentration of low molar mass acidic degradation products within the core of the filament 102. Although the filaments 102 shown in FIGS. 11A-C include specific shapes, the filaments 102 as discussed herein may include uneven, jagged, or polygonal sides, or include more or less sides than those shown in FIGS. 11A-C (e.g., a triangle, square, pentagon, hexagon). In certain instances, the filaments 102, as discussed herein, may be hollow (e.g., microtubing).

Figure 12:
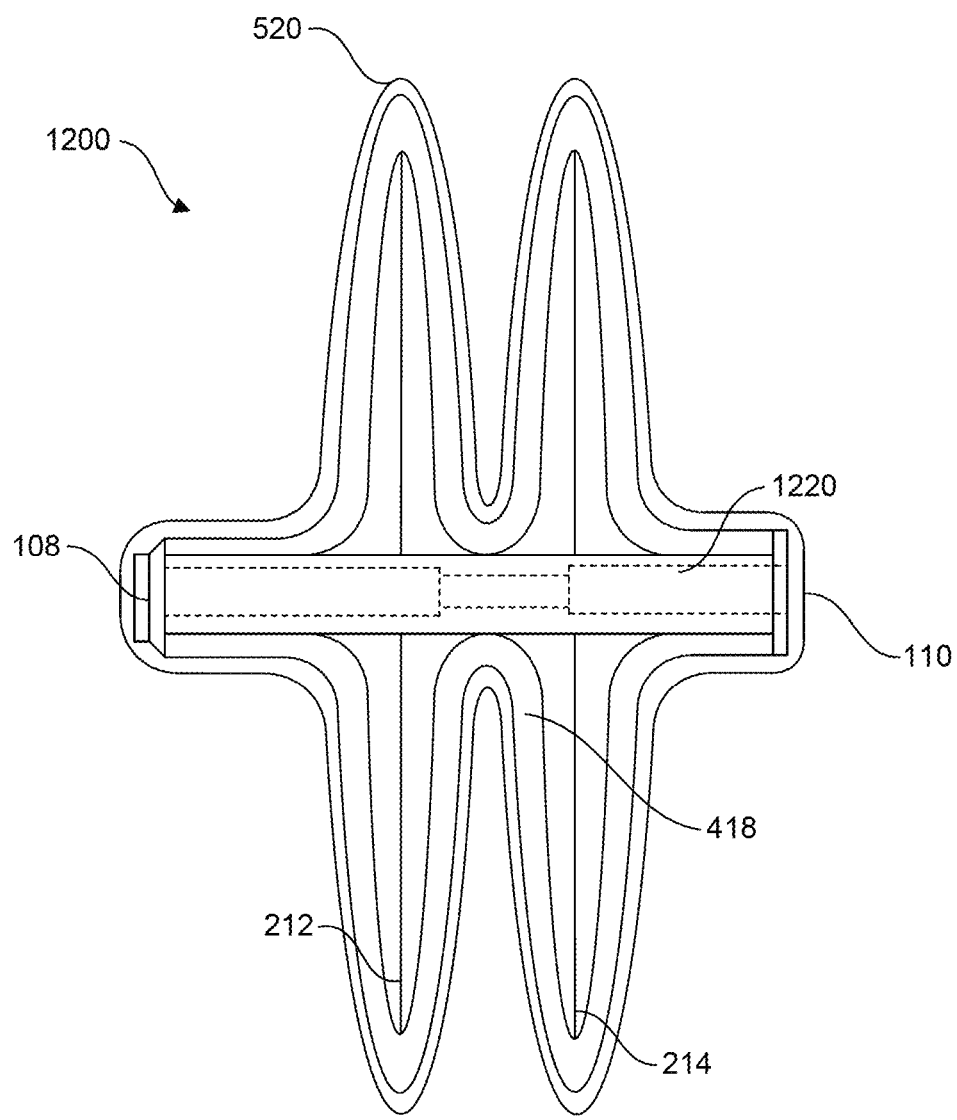
FIG. 12 is a side view of another example occluder with a membrane, in accordance with an embodiment.

FIG. 12 is a side view of another example occluder 1200 with a membrane, in accordance with an embodiment. The occluder 1200 with a membrane 520, in accordance with an embodiment. The membrane 520 may be arranged about a plurality of absorbable filaments (as discussed in detail above) and configured to contain fragments of the plurality of absorbable filaments in response to the fracture or degradation of the filament and promote tissue ingrowth into the membrane or tissue encapsulation of the membrane. In certain instances, the membrane 520 is configured to promote healthy tissue growth and remain with the tissue after degradation of the absorbable filaments. The filaments may form a proximal disk 212 and a distal disk 214.

The absorbable filaments (discussed and shown in detail above) are configured to structurally enhance or hold-open (or close) the space into which the occluder is implanted. The absorbable filaments prevent embolization of the device through the opening into which it is implanted (e.g., PFO) and are configured to apply appositional forces against the septum such that the membrane 520 may facilitate tissue ingrowth close to the opening or tissue encapsulation of the membrane 520. During degradation of the bio-degradable or bio-corrodible filaments, the membrane 520 facilitates healthy tissue ingrowth into the membrane 520, tissue regrowth, and/or tissue encapsulation of the membrane 520 such that the structure provided by the bio-degradable or bio-corrodible filaments may become unnecessary. The membrane 520 maintains within the patient and provides structure without a metallic structure remaining as would occur with a non-degradable stent.

A waist 418 may be formed of central portions of the plurality of absorbable filaments. In addition, the waist 418 may be configured to form an open central area within the plurality of absorbable filaments in each of the deployed and elongated configuration. The waist 418 may be configured to bring the proximal disk 212 into apposition with a first side of the tissue wall and the distal disk 214 into apposition with the second side of the tissue wall.

The occluder 1200 may also include hubs 108, 110. The hubs 108, 110 may be formed by the filaments or may include an additional band, eyelet, or material that crimps or holds the end portions of the filaments together. In certain instances, the end portions of the filaments may be bonded, melted, or otherwise formed together to the hubs 108, 110. Optionally, the membrane 520 may be attached during the formation of the hub.

In certain instances, the occluder 1200 may include a catch member 1220 arranged between the hubs 108, 110. The catch member 1220 may be configured to couple to a delivery catheter or delivery system. In certain instances, the catch member 1220 may include a threaded end that is configured to thread with a corresponding threaded member on the delivery catheter or delivery system. The catch member 1220 may facilitate deployment of the disks 212, 214. In certain instances, the catch member 1220 includes a union component that is attached to the hubs 108, 110. The catch member 1220 may draw the disks 212, 214 together and maintain apposition with the tissue when the occluder 1200 is deployed. The catch member 1220 may be formed from an absorbable material or other material (e.g., Nitinol). The catch member 1220 may be flexible in the mid-body portion to allow conformability of the disks 212, 214. In certain instances, the catch member 1220 may be spring loaded to maintain apposition of the disks 212, 214 with tissue. The catch member 1200 may be include a lumen through it to allow recrossability.

Figure 13A:
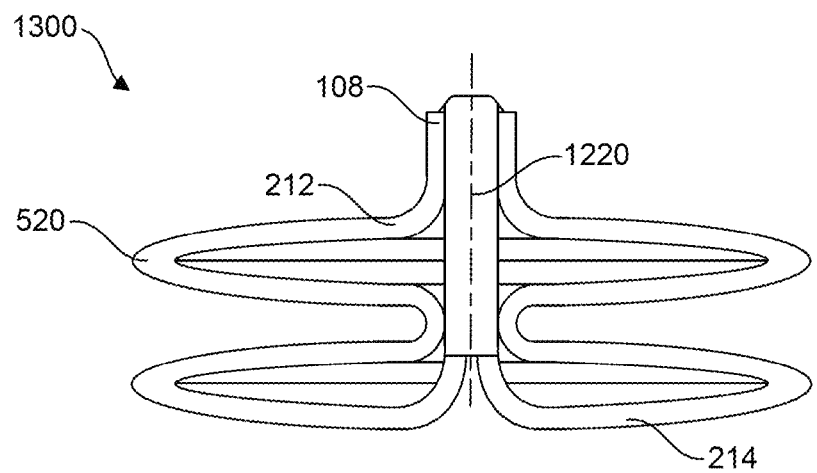
FIG. 13A is a view of another example occluder with a membrane and a catch member in a first configuration, in accordance with an embodiment.

FIG. 13A is a view of another example occluder 1300 with a membrane 520 and a catch member 1220 in a first configuration, in accordance with an embodiment. The occluder 1300 with a membrane 520, in accordance with an embodiment. The membrane 520 may be arranged about a plurality of absorbable filaments (as discussed in detail above) and configured to contain fragments of the plurality of absorbable filaments in response to the fracture or degradation of the filament and promote tissue ingrowth into the membrane 520 and/or tissue encapsulation of the membrane 520. In certain instances, the membrane 520 is configured to promote healthy tissue growth and remain with the tissue after degradation of the absorbable filaments. The filaments may form a proximal disk 212 and a distal disk 214.

The absorbable filaments (discussed and shown in detail above) are configured to structurally enhance or hold-open or close the space into which the occluder is implanted. The absorbable filaments prevent embolization of the device through the opening into which it is implanted (e.g., PFO) and are configured to apply appositional forces against the septum such that the membrane 520 may facilitate tissue ingrowth close to the opening or tissue encapsulation of the membrane 520. During degradation of the bio-degradable or bio-corrodible filaments, the membrane 520 facilitates healthy tissue ingrowth or regrowth (and/or tissue encapsulation of the membrane 520) such that the structure provided by the bio-degradable or bio-corrodible filaments may become unnecessary. The membrane 520 maintains within the patient and provides structure without a metallic structure remaining as would occur with a non-degradable stent.

Figure 13B:
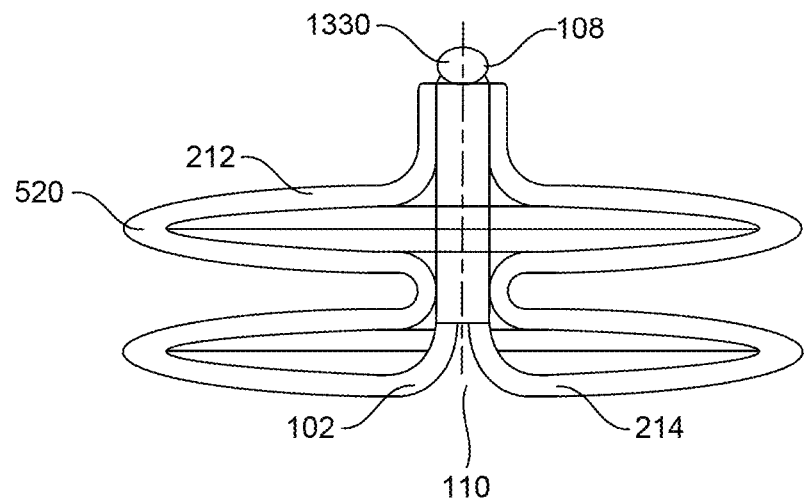
FIG. 13B is the occluder, shown in FIG. 13A, in a second configuration, in accordance with an embodiment.

Ends 108, 110 of the occluder may be formed by the filaments or may include an additional band, eyelet, or material that crimps or holds the end portions of the filaments together. As shown in FIG. 13B, a distal end 110 of the occluder 1330 is inverted such that the filaments 102 extend inwardly and back toward a proximal end 108. As shown in FIG. 13A, the occluder 1300 may include a catch member 1220 arranged within the proximal end 108 to couple to a delivery catheter or delivery system.

As shown in FIG. 13B, the proximal end 108 may include a ball 1330. The ball 1330 may be absorbable (or may be a barb feature). The ball 1330 may facilitate capturing of the occluder 1300 after delivery or otherwise block a pathway through the occluder 1300.

Figure 14A:
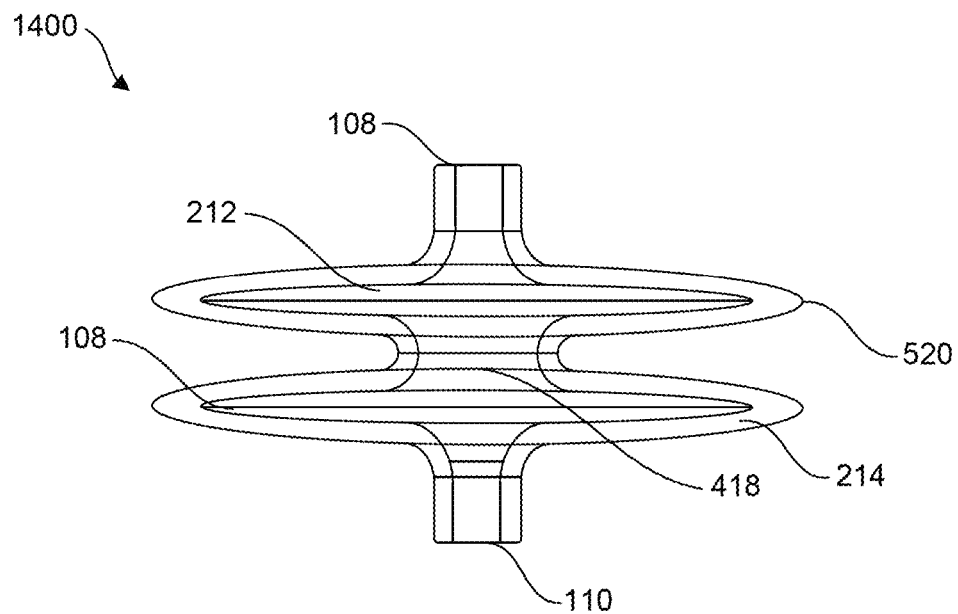
FIG. 14A is a view of another example occluder with a membrane, in accordance with an embodiment.
Figure 14B:
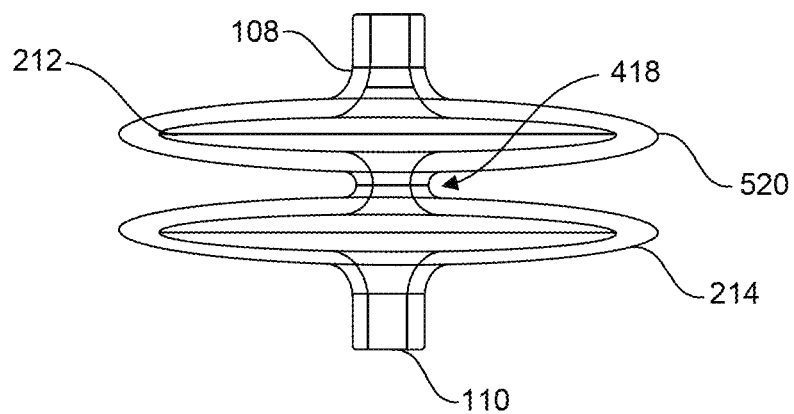
FIG. 14B is the occluder, shown in FIG. 14A, with a different waist configuration, in accordance with an embodiment.

FIG. 14A is a view of another example occluder 1400 with a membrane 520, in accordance with an embodiment. FIG. 14B is the occluder 1400, shown in FIG. 14A, with a different waist configuration 418, in accordance with an embodiment. The differing waist 418 diameters may be related to the target location of the occluder 1400. For example, when placed within an atrial septal defect (ASD), the occluder 1400 may include a larger waist as shown in FIG. 14A. When placed within a patent foramen ovale (PFO), the occluder 1400 may include a smaller waist as shown in FIG. 14B.

As discussed in detail above, the occluder 1400 includes a membrane 520 that may be arranged about a plurality of absorbable filaments (as discussed in detail above) and configured to contain fragments of the plurality of absorbable filaments in response to the fracture or degradation of the filament and promote tissue ingrowth into the membrane and/or tissue encapsulation of the membrane 520 and/or healthy tissue regrowth. In certain instances, the membrane 520 is configured to promote healthy tissue growth and remain with the tissue after degradation of the absorbable filaments. The filaments may form a proximal disk 212 and a distal disk 214.

The absorbable filaments (discussed and shown in detail above) are configured to structurally enhance or hold-open the space into which the occluder is implanted. The absorbable filaments prevent embolization of the device through the opening into which it is implanted (e.g., PFO) and are configured to apply appositional forces against the septum such that the membrane 520 may facilitate tissue ingrowth close to the opening and/or tissue encapsulation of the membrane 520 and/or healthy tissue regrowth. During degradation of the bio-degradable or bio-corrodible filaments, the membrane 520 facilitates healthy tissue ingrowth or regrowth such that the structure provided by the bio-degradable or bio-corrodible filaments may become unnecessary. The membrane 520 maintains within the patient and provides structure without a metallic structure remaining as would occur with a non-degradable stent.

The occluder 1400 may also include hubs 108, 110. The hubs 108, 110 may be formed by the filaments or may include an additional band, eyelet, or material that crimps or holds the end portions of the filaments together. In certain instances, the end portions of the filaments may be bonded, melted, or otherwise formed together to the hubs 108, 110. Optionally, the membrane 520 may be attached during the formation of the hub.

Figure 15:
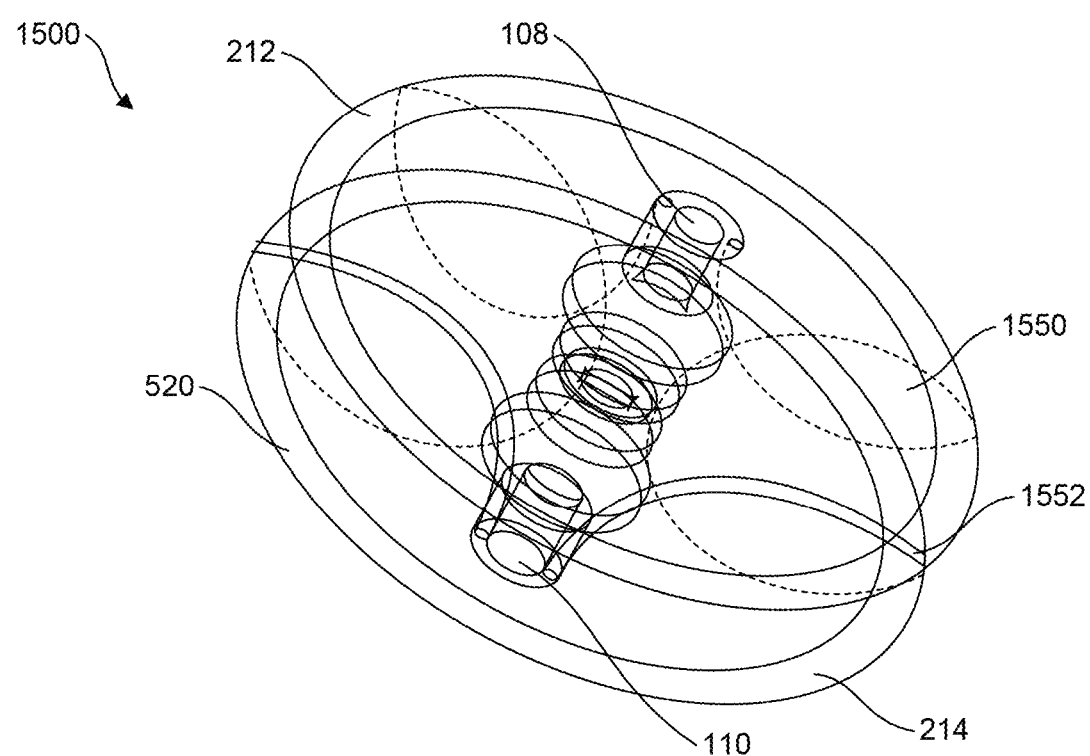
FIG. 15 is a perspective view of another example occluder with a membrane, in accordance with an embodiment.

FIG. 15 is a perspective view of another example occluder 1500 with a membrane 520, in accordance with an embodiment. As discussed in detail above, the occluder 1500 includes a membrane 520 that may be arranged about a plurality of absorbable filaments (as discussed in detail above) and configured to contain fragments of the plurality of absorbable filaments in response to the fracture or degradation of the filament and promote tissue ingrowth into the membrane or tissue encapsulation of the membrane 520. In certain instances, the membrane 520 is configured to promote healthy tissue growth and remain with the tissue after degradation of the absorbable filaments. The filaments may form a proximal disk 212 and a distal disk 214.

The absorbable filaments (discussed and shown in detail above) are configured to structurally enhance or hold-open the space into which the occluder is implanted. The absorbable filaments prevent embolization of the device through the opening into which it is implanted (e.g., PFO) and are configured to apply appositional forces against the septum such that the membrane 520 may facilitate tissue ingrowth close to the opening. During degradation of the bio-degradable or bio-corrodible filaments, the membrane 520 facilitates healthy tissue ingrowth or regrowth (or tissue encapsulation of the membrane 520) such that the structure provided by the bio-degradable or bio-corrodible filaments may become unnecessary. The membrane 520 maintains within the patient and provides structure without a metallic structure remaining as would occur with a non-degradable stent.

The occluder 1500 may also include hubs 108, 110. The hubs 108, 110 may be formed by the filaments or may include an additional band, eyelet, or material that crimps or holds the end portions of the filaments together. In certain instances, the end portions of the filaments may be bonded, melted, or otherwise formed together to the hubs 108, 110. Optionally, the membrane 520 may be attached during the formation of the hub.

In certain instances and as shown, the occluder 1500 may include radiopaque elements 1550, 1552. The radiopaque elements 1550, 1552 may be arranged within the disks 212, 214. In certain instances, radiopaque elements 1550, 1552 extend from the hubs 108, 110 to a perimeter of the disks 212, 214. The radiopaque elements 1550, 1552 may be formed of or include a radiopaque material (e.g., gold, tantalum, iodine, or a combination thereof). In certain instances, the radiopaque elements 1550, 1552 may be filaments wrapped in a membrane 520 material. The radiopaque elements 1550, 1552 may be sputter coated or spray coated to encapsulate the radiopaque material within the membrane 520 material.

Figure 16:
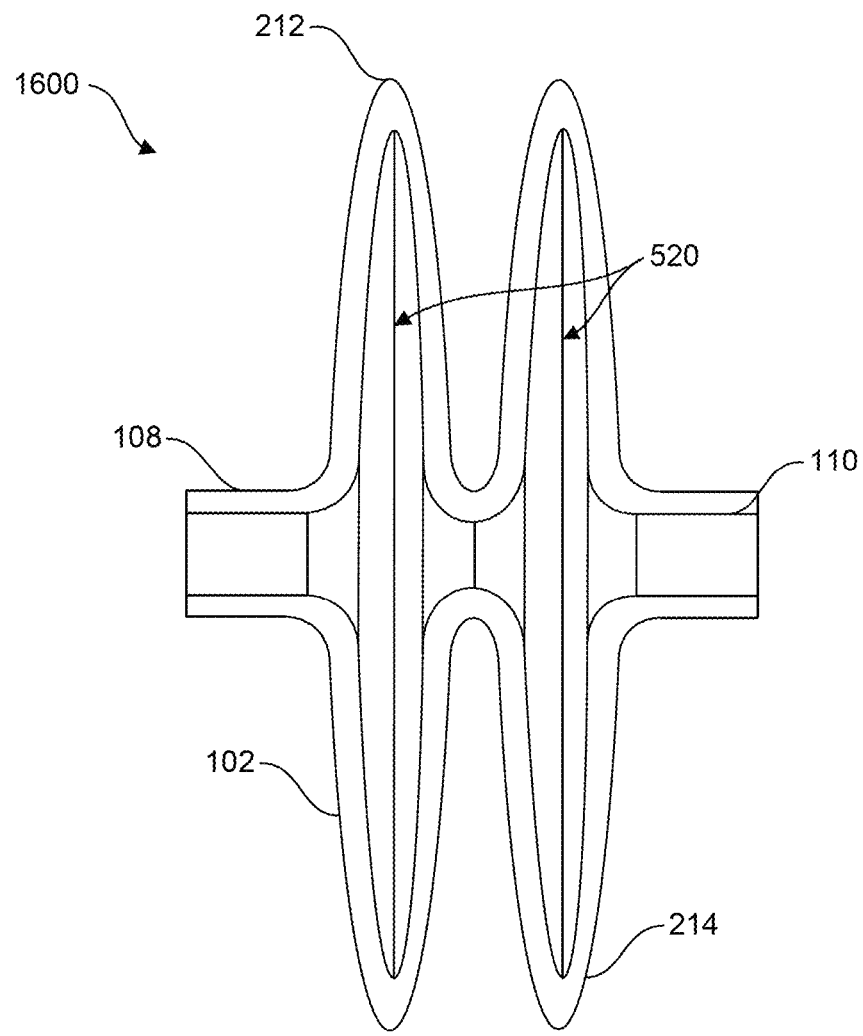
FIG. 16 is a side view of another example occluder, in accordance with an embodiment.

FIG. 16 is a side view of another example occluder 1600, in accordance with an embodiment. As discussed in detail above, the occluder 1600 includes a membrane 520 that may be arranged individually about each of a plurality of absorbable filaments 102 (as discussed in detail above) and configured to contain fragments of the plurality of absorbable filaments 102 in response to the fracture or degradation of the filament 102 and promote tissue ingrowth into the membrane or tissue encapsulation of the membrane 520. In certain instances, the membrane 520 is configured to promote healthy tissue growth and remain with the tissue after degradation of the absorbable filaments. The filaments 102 may form a proximal disk 212 and a distal disk 214.

The absorbable filaments 102 are configured to structurally enhance or hold-open the space into which the occluder 1600 is implanted. The absorbable filaments 102 prevent embolization of the device through the opening into which it is implanted (e.g., PFO) and are configured to apply appositional forces against the septum. In certain instances, membrane components 520 also be arranged within the disks 212, 214 to may facilitate tissue ingrowth close to the opening. During degradation of the bio-degradable or bio-corrodible filaments 102, the membrane components 520 within the disks 212, 214 facilitate healthy tissue ingrowth or regrowth such that the structure provided by the bio-degradable or bio-corrodible filaments may become unnecessary. The membrane 520 arranged individually about the filaments 102 and the membrane components 520 within the disks 212, 214 stay within the patient and provides structure without a metallic structure remaining as would occur with a non-degradable stent.

The occluder 1600 may also include hubs 108, 110. The hubs 108, 110 may be formed by the filaments or may include an additional band, eyelet, or material that crimps or holds the end portions of the filaments together. In certain instances, the end portions of the filaments may be bonded, melted, or otherwise formed together to the hubs 108, 110. Optionally, the membrane 520 may be attached during the formation of the hub.

Figure 17:
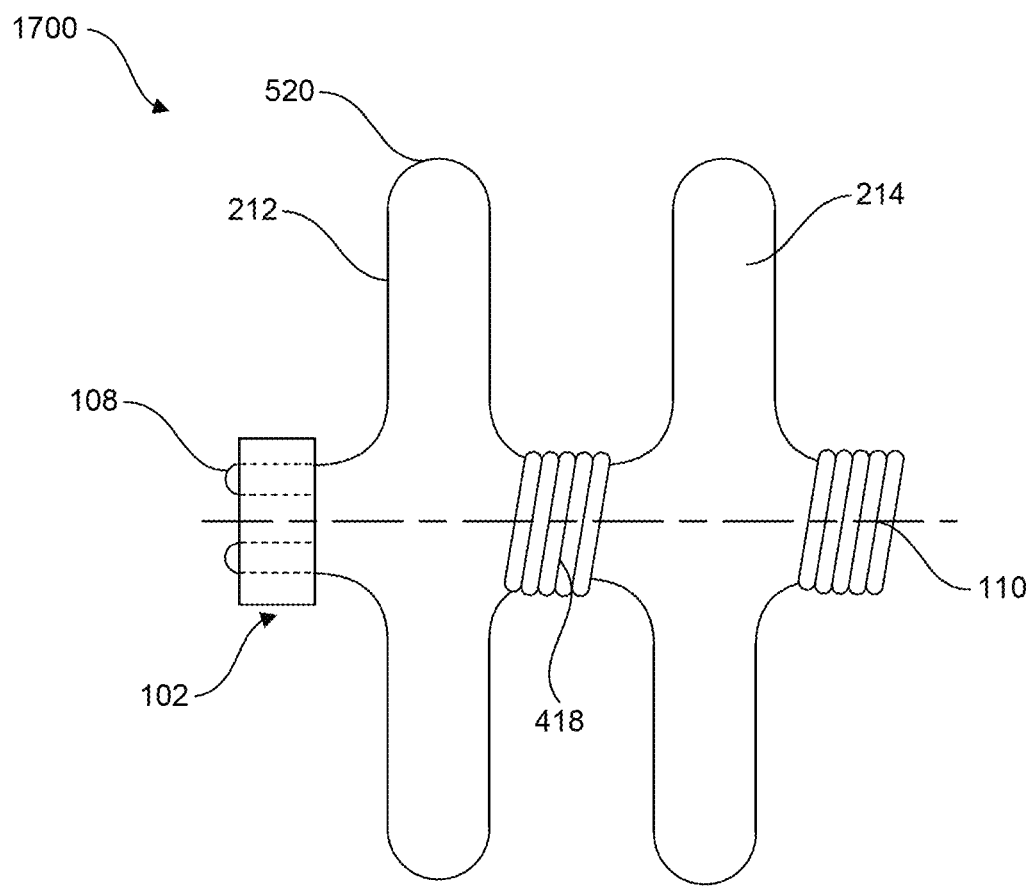
FIG. 17 is a side view of another example occluder with a membrane, in accordance with an embodiment.

FIG. 17 is a side view of another example occluder 1700 with a membrane 520, in accordance with an embodiment. As discussed in detail above, the occluder 1700 includes a membrane 520 that may be arranged about a plurality of absorbable filaments 102 (as discussed in detail above) and configured to contain fragments of the plurality of absorbable filaments 102 in response to the fracture or degradation of the filament 102 and promote tissue ingrowth into the membrane 520 or tissue encapsulation of the membrane 520. In certain instances, the membrane 520 is configured to promote healthy tissue growth and remain with the tissue after degradation of the absorbable filaments 102. The filaments 102 may form a proximal disk 212 and a distal disk 214.

The absorbable filaments 102 (discussed and shown in detail above) are configured to structurally enhance or hold-open the space into which the occluder is implanted. The absorbable filaments 102 prevent embolization of the device through the opening into which it is implanted (e.g., PFO) and are configured to apply appositional forces against the septum such that the membrane 520 may facilitate tissue ingrowth close to the opening. During degradation of the bio-degradable or bio-corrodible filaments 102, the membrane 520 facilitates healthy tissue ingrowth or regrowth (or tissue encapsulation of the membrane 520) such that the structure provided by the bio-degradable or bio-corrodible filaments 102 may become unnecessary. The membrane 520 maintains within the patient and provides structure without a metallic structure remaining as would occur with a non-degradable stent.

The occluder 1700 may also include hubs 108, 110. The hubs 108, 110 may be formed by the filaments 102 or may include an additional band, eyelet, or material that crimps or holds the end portions of the filaments 102 together. In certain instances, the end portions of the filaments 102 may be bonded, melted, or otherwise formed together to the hubs 108, 110. Optionally, the membrane 520 may be attached during the formation of the hub. In certain instances, one or more of the hubs 108, 110 and waist 418 may be formed by a ring (as shown by hub 108) or a winding of the filaments 102 (as shown by waist 4189 and hub 110).

Figure 18:
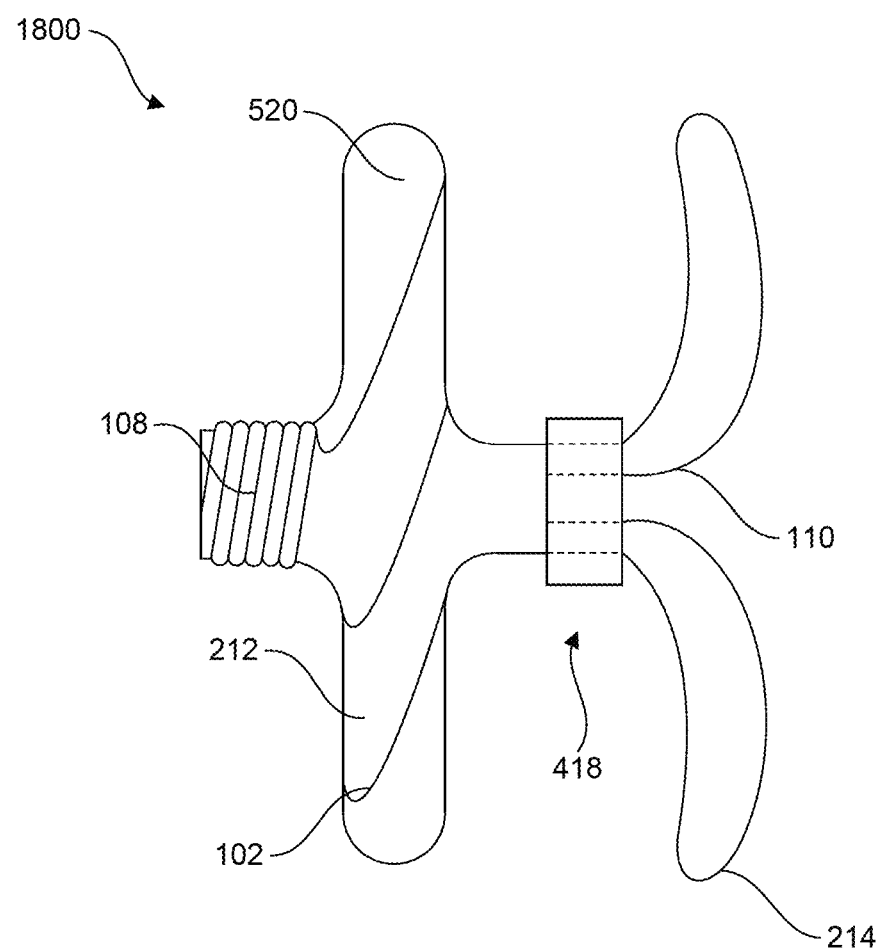
FIG. 18 is a side view of another example occluder with a membrane, in accordance with an embodiment.

FIG. 18 is a side view of another example occluder with a membrane, in accordance with an embodiment. As discussed in detail above, the occluder 1800 includes a membrane 520 that may be arranged about a plurality of absorbable filaments 102 (as discussed in detail above) and configured to contain fragments of the plurality of absorbable filaments 102 in response to the fracture or degradation of the filament and promote tissue ingrowth into the membrane. In certain instances, the membrane 520 is configured to promote healthy tissue growth and remain with the tissue after degradation of the absorbable filaments 102. The filaments 102 may form a proximal disk 212 and a distal disk 214.

The absorbable filaments 102 (discussed and shown in detail above) are configured to structurally enhance or hold-open the space into which the occluder is implanted. The absorbable filaments 102 prevent embolization of the device through the opening into which it is implanted (e.g., PFO) and are configured to apply appositional forces against the septum such that the membrane 520 may facilitate tissue ingrowth close to the opening or tissue encapsulation of the membrane 520. During degradation of the bio-degradable or bio-corrodible filaments 102, the membrane 520 facilitates healthy tissue ingrowth or regrowth such that the structure provided by the bio-degradable or bio-corrodible filaments 102 may become unnecessary. The membrane 520 maintains within the patient and provides structure without a metallic structure remaining as would occur with a non-degradable stent.

The occluder 1800 may also include a proximal end 108 and a distal end 110, 110. The ends 108, 110 may be formed by the filaments 102 or may include an additional band, eyelet, or material that crimps or holds the end portions of the filaments 102 together. In certain instances, the end portions of the filaments 102 may be bonded, melted, or otherwise formed together to the hubs 108, 110. Optionally, the membrane 520 may be attached during the formation of the hub. The filaments 102 may be helically wound and one or more of the disks 212, 214 may be a closed-loop as is shown by disk 214 and therefore there is no hub at a distal end 110. In addition, waist 418 may include a ring to constrain the waist 418 portion.

Figure 19:
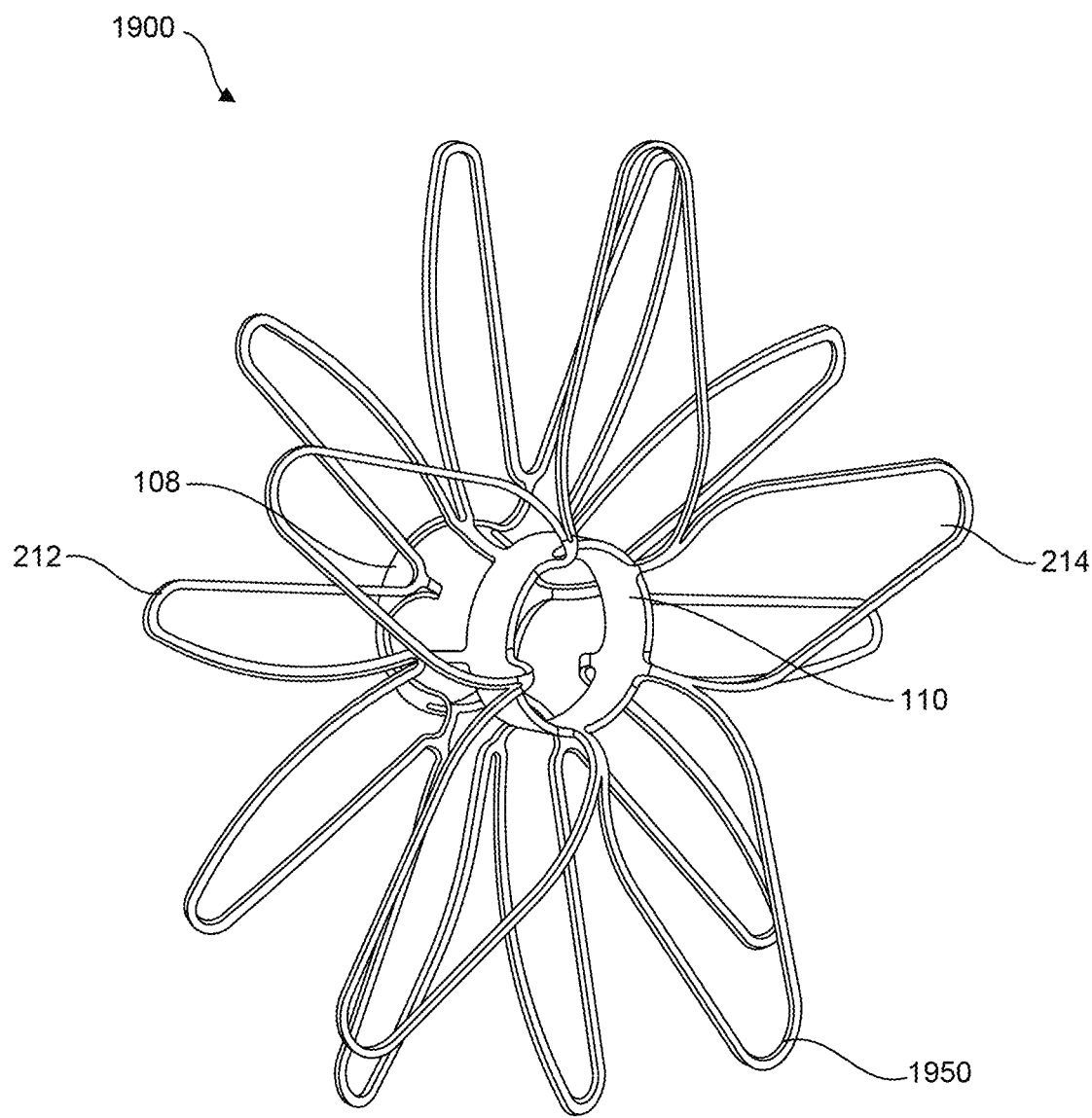
FIG. 19 is a perspective view of an example frame that may be used in an occluder, in accordance with an embodiment.

FIG. 19 is a perspective view of an example frame 1900 that may be used in an occluder, in accordance with an embodiment. As shown, the frame 1900 includes disks 212, 214 and hubs 108, 110. Each of the disks 212, 214 may include a plurality of petals 1950 that converge at the hubs 212, 214. The hubs 108, 110 may be cylindrical. The frame 1900 is formed from a cut-pattern (tube or sheath) of an absorbable material. The frame 1900 may be extruded and quenched to shape set the frame 1900 in the pattern shown. The frame 1900 may be considered to include a plurality of struts or filaments formed by the cut-pattern. The frame 1900 may be considered to include a plurality of struts or filaments formed by the cut-pattern.

Figure 20A:
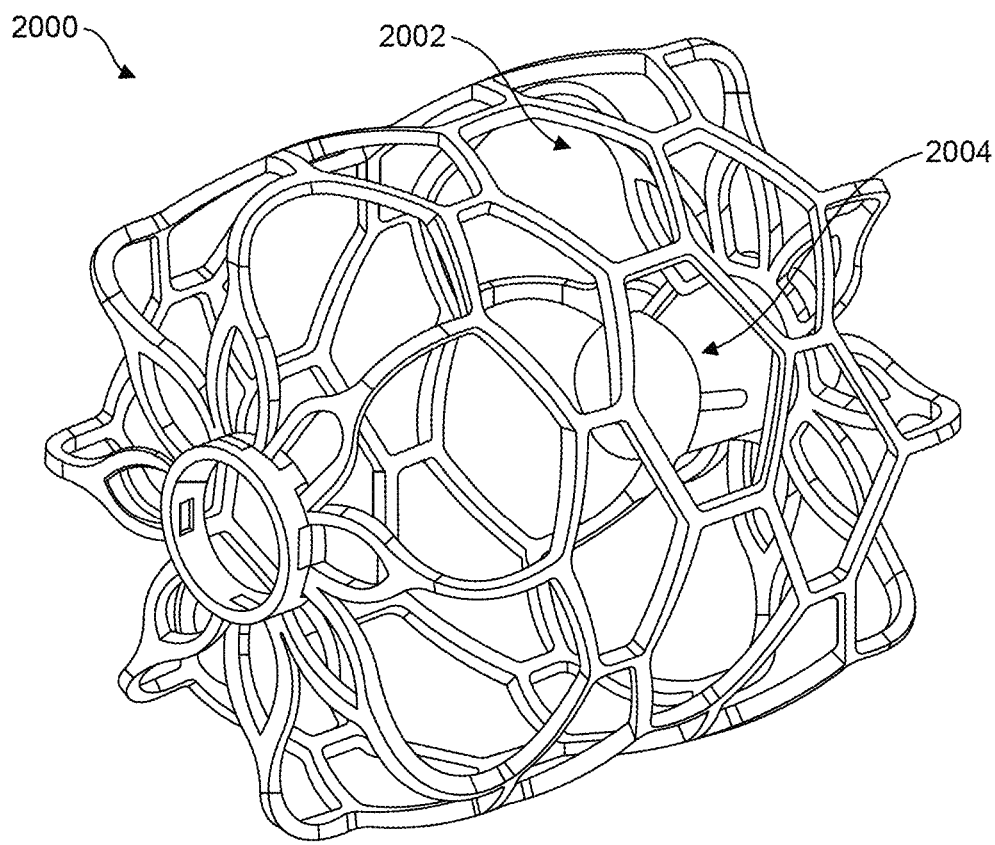
FIG. 20A a first perspective view of an example frame that may be used in an occluder, in accordance with an embodiment.
Figure 20B:
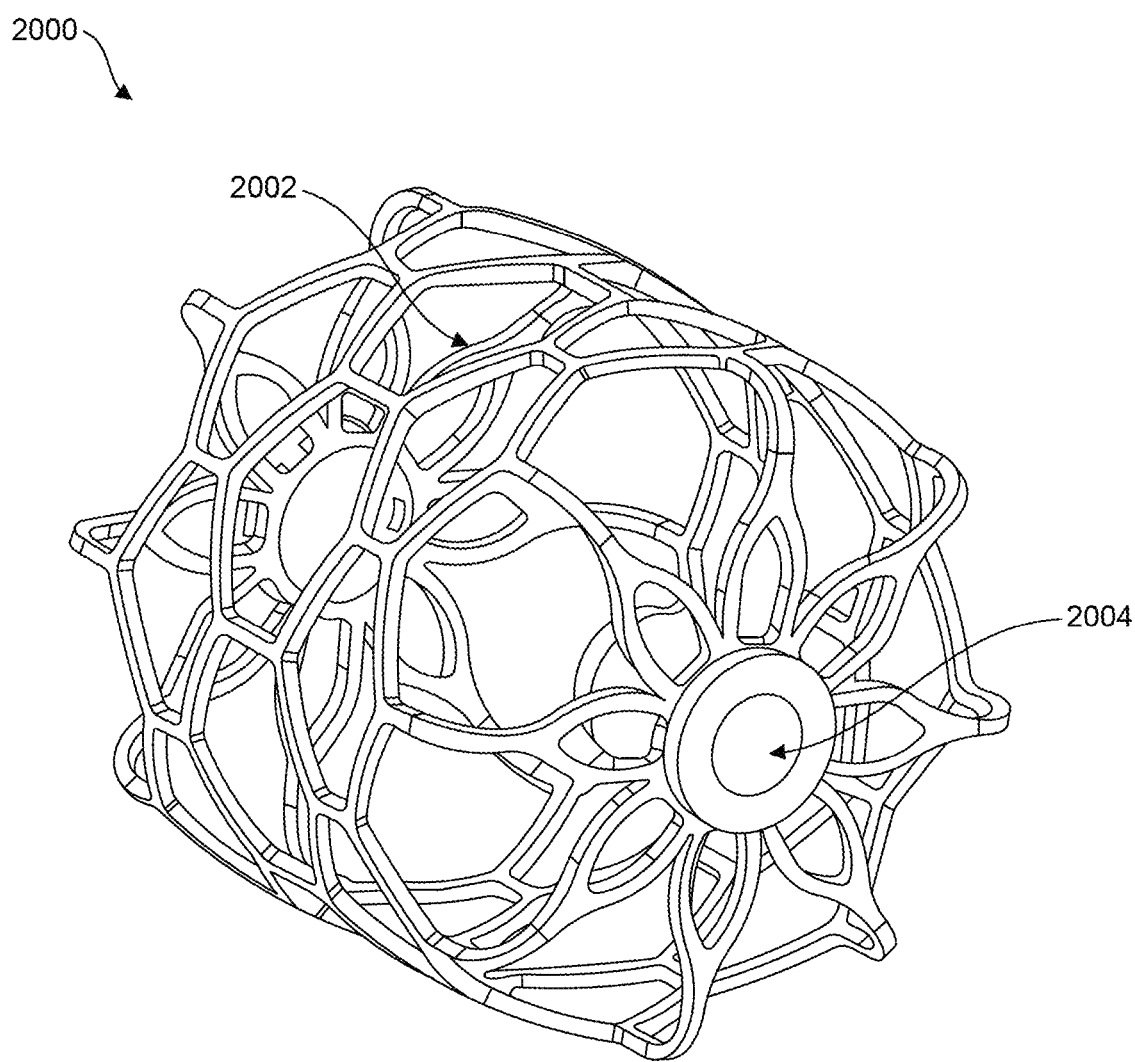
FIG. 20B a second perspective view of the frame, shown in FIG. 20A, in accordance with an embodiment.

FIG. 20A a first perspective view of an example frame 2000 that may be used in an occluder and FIG. 20B a second perspective view of the frame 2000, shown in FIG. 20A, in accordance with an embodiment. As shown, the frame 2000 forms a plug structure formed of a cut-pattern (tube or sheath) of an absorbable material. The plug structure may include a plurality of cells 2002 that may include a polygonal shape. The frame 2000 may be a bioabsorbable support structure and include a membrane (not shown) arranged about the support structure as described in detail above. A plug 2004 may be arranged within the frame 2000 at one or both ends. The plug 2004 may be degradable and interface with a delivery catheter or system. In certain instances, the frame 2000 may be used a vascular plug or as an occluder in other portions of the body such as an appendage (e.g., left atrial appendage). The frame 2000 may be used to seal cardiac and vascular defects or tissue opening, the vascular system, or other location within a patient. The frame 2000 (and other frame discussed herein) is a scaffold or bioabsorbable support structure. The frame 2000 may be considered to include a plurality of struts or filaments formed by the cut-pattern.

Figure 21:
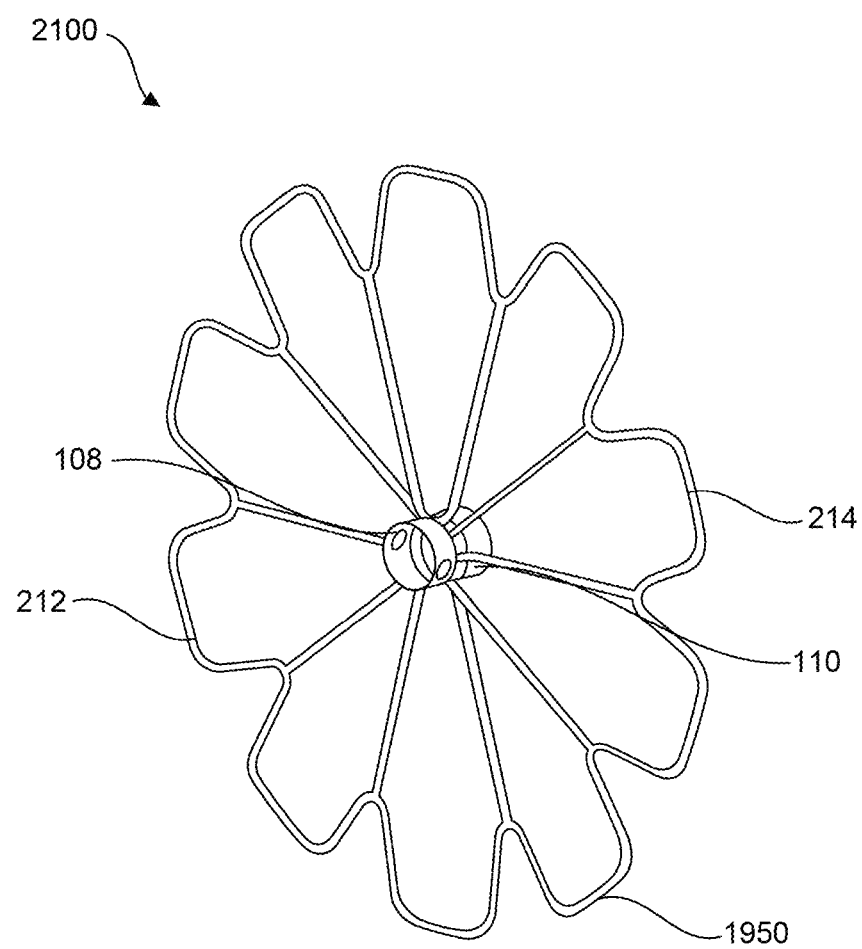
FIG. 21 is a perspective view of an example frame that may be used in an occluder, in accordance with an embodiment.

FIG. 21 is a perspective view of an example frame that may be used in an occluder, in accordance with an embodiment. As shown, the frame 2100 includes disks 212, 214 and hubs 108, 110. Each of the disks 212, 214 may include a plurality of petals 1950 that converge at the hubs 212, 214. The hubs 108, 110 may be cylindrical. The frame 2100 is formed from a cut-pattern (tube or sheath) of an absorbable material. The frame 2100 may be extruded and quenched to shape set the frame 2100 in the pattern shown. In other instances, the frame 2100 may be formed from additive printing or additive manufacturing. The frame 2100 may be considered to include a plurality of struts or filaments formed by the cut-pattern. The frame 2100 may be considered to include a plurality of struts or filaments formed by the cut-pattern. The frame 2100 may be injected molded or formed by additive printing.

Figure 22:
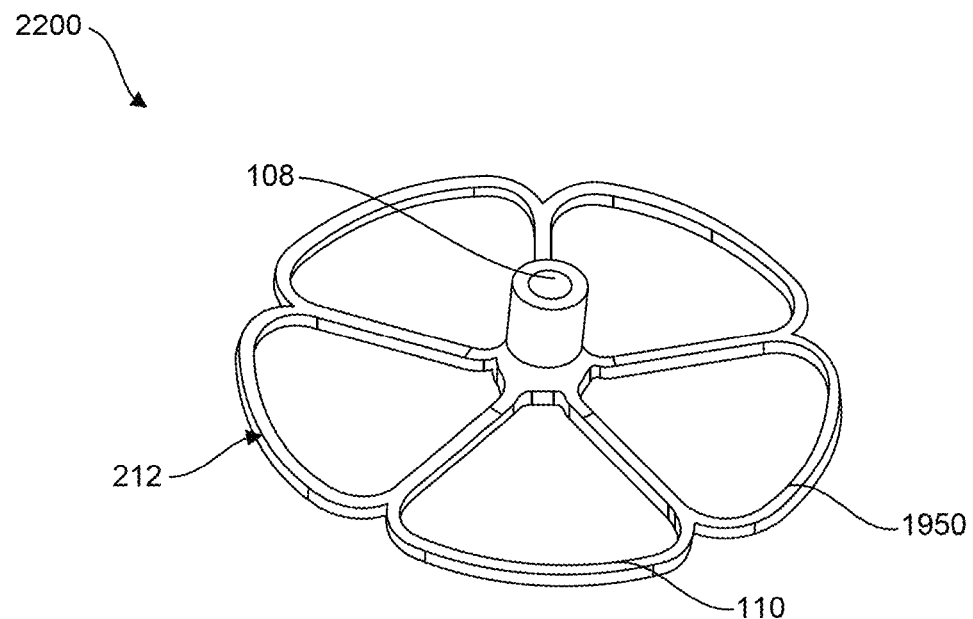
FIG. 22 is a perspective view of an example frame that may be used in an occluder, in accordance with an embodiment.

FIG. 22 is a perspective view of an example frame 2200 that may be used in an occluder, in accordance with an embodiment. As shown, the frame 2100 includes disks 212, 214 and hubs 108, 110. Each of the disks 212, 214 may include a plurality of petals 1950 that converge at the hubs 212, 214. The hubs 108, 110 may be cylindrical. The frame 2100 is formed from a cut-pattern (tube or sheath) of an absorbable material. The frame 2100 may be extruded and quenched to shape set the frame 2100 in the pattern shown. In other instances, the frame 2200 may be formed from additive printing or additive manufacturing. The frame 2200 may be considered to include a plurality of struts or filaments formed by the cut-pattern. The frame 2200 may be considered to include a plurality of struts or filaments formed by the cut-pattern. The frame 2200 may be injected molded or formed by additive printing.

Figure 23:
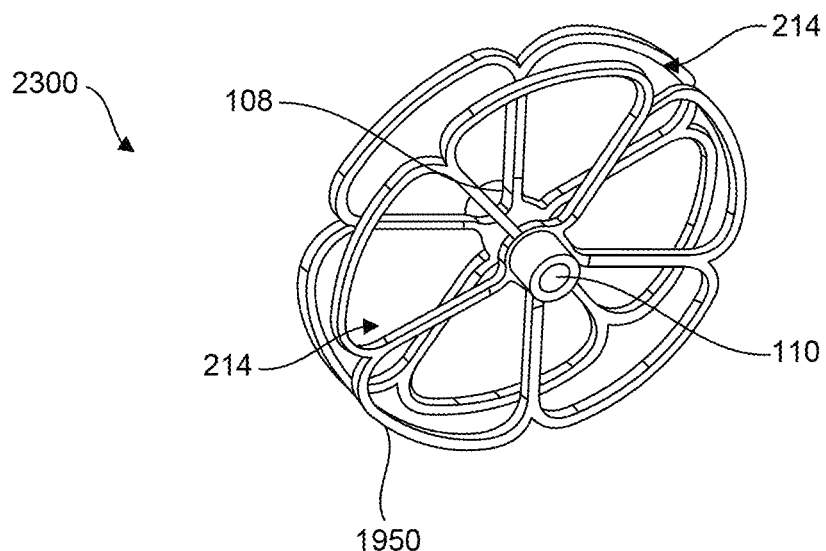
FIG. 23 is a perspective view of an example frame that may be used in an occluder, in accordance with an embodiment.
Figure 24:
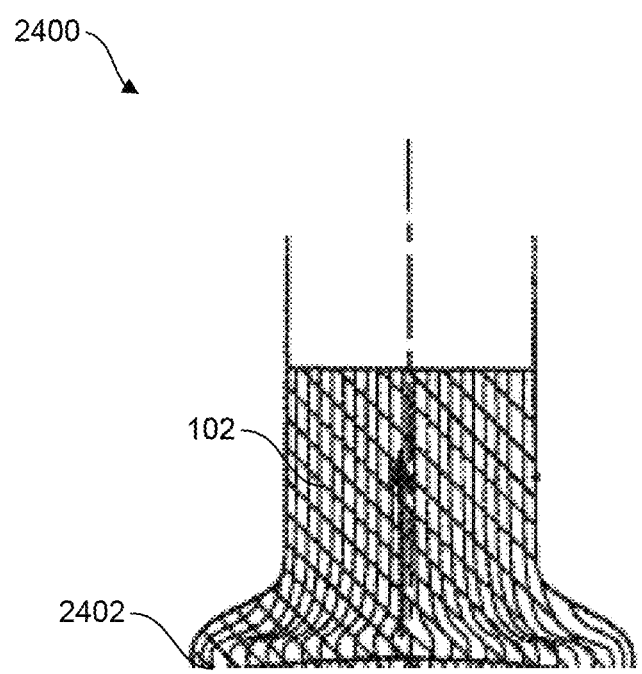
FIG. 24 shows an example medical device, in accordance with an embodiment.

FIG. 23 is a perspective view of an example frame 2300 that may be used in a medical device, in accordance with an embodiment. As shown, the frame 2100 includes one disk 212 and a hub 108. FIG. 24 shows an example frame 2400 that includes two disks 212, 214 formed by the frame 2300. Each of the one or two disks 212, 214 may include a plurality of petals 1950 that converge at the hubs 212, 214. The hubs 108, 110 may be cylindrical. The frames 2200, 2300 may be formed from a cut-pattern (tube or sheath) of an absorbable material. The frame frames 2200, 2300 may be extruded and quenched to shape set the frames 2200, 2300 in the pattern shown. In other instances, the frames 2200, 2300 may be formed from additive printing or additive manufacturing. The frame 2300 may be considered to include a plurality of struts or filaments formed by the cut-pattern. The frame 2300 may be considered to include a plurality of struts or filaments formed by the cut-pattern. The frame 2300 may be injected molded or formed by additive printing.

FIG. 24 shows an example medical device 2400, in accordance with an embodiment. The medical device 2400 may be a fistula device 2400. The fistula device 2400 is formed from absorbable filaments 102 and may include a flange 2402 at one or both ends. As shown, the flange 2402 is arranged at one end of the fistula device 2400. The fistula device 2400 offers support while the fistula matures and becomes flaccid over time as described in detail above relative to the occluders discussed herein. The fistula device 2400 may include a membrane (not shown) arranged about the filaments 102.

Figure 25:
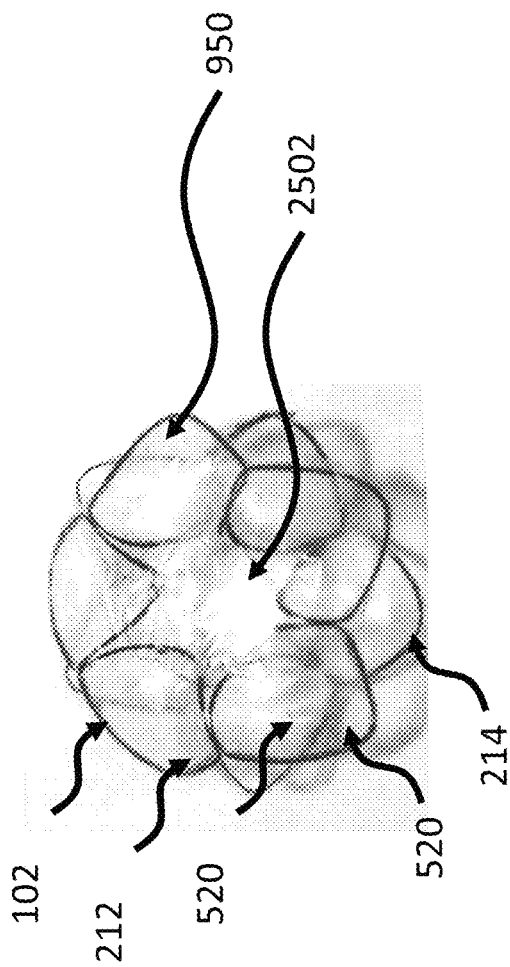
FIG. 25 shows an example medical device, in accordance with an embodiment.

FIG. 25 shows an example medical device 2500, in accordance with an embodiment. The medical device 2500 may be a shunt device 2500. The shunt device 2500 may be formed of absorbable filaments 102 and a membrane 520 as described in detail above. The shunt device 2500 may include a passageway 2502 arranged centrally between disks 212, 214. Each of the disks may include petals 950 that may conform to a tissue wall. In certain instances, the shunt device 2500 may be implanted at an access site or within tissue and the promote tissue healing.

As described above, the membrane 520 may be arranged about the filaments 102 and configured to contain fragments of the plurality of absorbable filaments 102 in response to the fracture or degradation of the filament 102 and promote tissue ingrowth into the membrane 520 or tissue encapsulation of the membrane 520. In certain instances, the membrane 520 is configured to promote healthy tissue growth or tissue encapsulation of the membrane 520 and remain with the tissue after degradation of the absorbable filaments 102. The tissue ingrowth or encapsulation and the membrane 520 remaining after degradation of the filaments 102 may allow for recrossability for further procedures if necessary.

Figure 26:
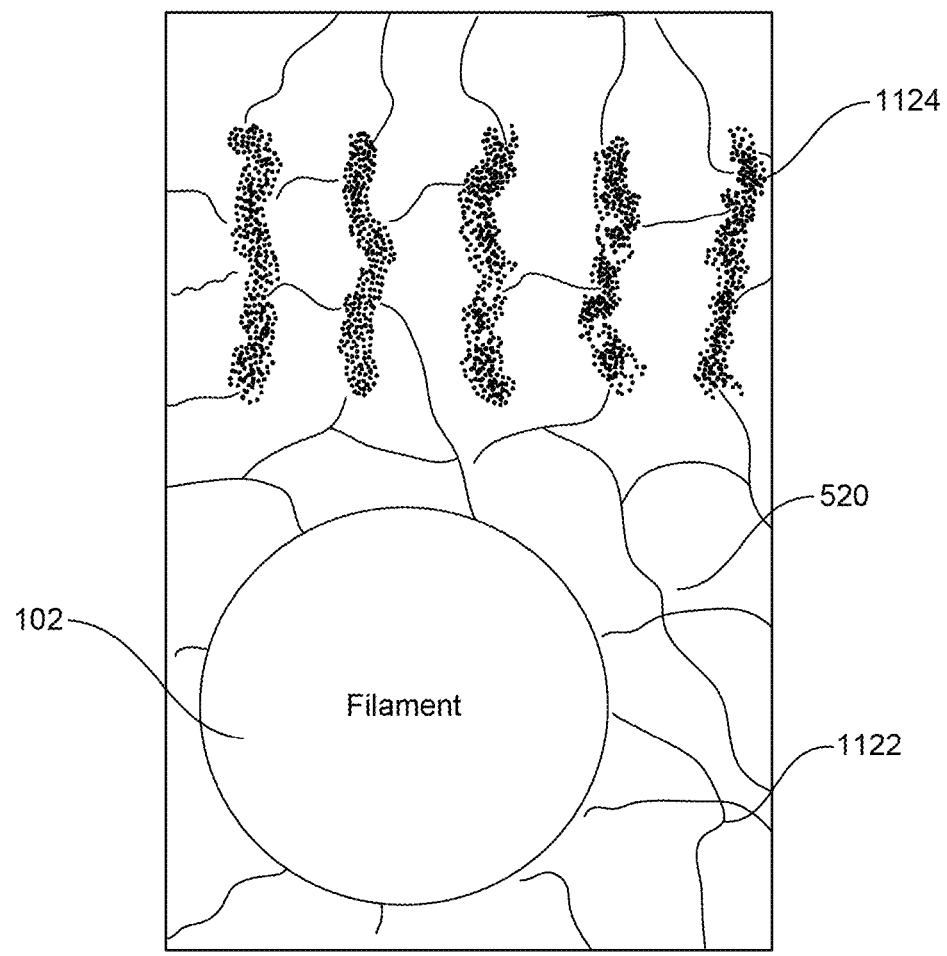
FIG. 26 shows an example stabilization of fragments of an example filament, in accordance with an embodiment.

FIG. 26 shows an example stabilization of fragments of an example filament 102, in accordance with an embodiment. As shown in FIG. 26, a membrane 520, may be formed of a scaffold structure (e.g., woven, knitted, non-woven, absorbable, or non-absorbable) components 1122, 1124. The components 1122, 1124 may contain structural components and fragments as the filament 102 degrades. In certain instances, the components 1122, 1124 may also include a porosity to stabilize the fragments and/or particles that may generate from the degrading of the filaments 102 100 and/or membrane 520. In certain instances, for example, underlying components 1122 may degrade and overlaying components 1124 may stabilize the underlying components 1122. In this manner, the membrane 520 may also degrade and facilitate stabilization as described in detail above.

Upon degradation, the underlying components 1122 may stabilizing the filament 102 and the overlying components 1124. The physical reduction of the overall structural may facilitate degradation of both the filament 102 and portions of the membrane 520 while also integrating the membrane 520 into tissue. The overlying components 1124 may degrade and the underlying components 1122 may integrate into the tissue. The overlying components 1124 degrading (or only the filament 102 degrading with the membrane 520 being non-degradable it its entirety) may facilitate continued tissue coverage and maturation. The overlying components 1124 and the underlying components 1122 may form a continuous membrane 520 or the overlying components 1124 and the underlying components 1122 may be separate structures. In the instances where the overlying components 1124 and the underlying components 1122 are separate structures, the overlying components 1124 may be the membrane 1202 and the underlying components 1122 may be an absorbable layer.

Examples of absorbable filaments include, but are not limited to absorbable metals such as magnesium and magnesium alloys, ferrous materials such as iron, aluminum and aluminum alloys, and other similar materials.

Examples of absorbable polymers that could be used either in the filament or in the membrane component include, but are not limited to, polymers, copolymers (including terpolymers), and blends that may include, in whole or in part, polyester amides, polyhydroxyalkanoates (PHA), poly(3-hydroxyalkanoates) such as poly(3-hydroxypropanoate), poly(3-hydroxybutyrate), poly(3-hydroxyvalerate), poly(3-hydroxyhexanoate), poly(3-hydroxyheptanoate) and poly(3-hydroxyoctanoate), poly(4-hydroxyalkanaote) such as poly(4-hydroxybutyrate), poly(4-hydroxyvalerate), poly (4-hydroxyhexanote), poly(4-hydroxyheptanoate), poly(4-hydroxyoctanoate) poly(L-lactide-co-glycolide) and copolymeric variants, poly(D,L-lactide), poly(L-lactide), polyglycolide, poly(D,L-lactide-co-glycolide), poly(L-lactide-co-glycolide), polycaprolactone, poly(lactide-co-caprolactone), poly(glycolid-caprolactone), poly(dioxanone), poly(ortho esters), poly(trimethylene carbonate), polyphosphazenes, poly(anhydrides), poly(tyrosine carbonates) and derivatives thereof, poly(tyrosine ester) and derivatives thereof, poly(imino carbonates), poly(lactic acid-trimethylene carbonate), poly(glycolic acid-trimethylene carbonate), polyphosphoester, polyphosphoester urethane, poly(amino acids), poly(ethylene glycol) (PEG), copoly(ether-esters) (e.g. PEO/PLA), polyalkylene oxides such as poly(ethylene oxide), poly(propylene oxide), poly(ether ester), polyalkylene oxalates, poly(aspirin), biomolecules such as collagen, chitosan, alginate, fibrin, fibrinogen, cellulose, starch, collagen, dextran, dextrin, fragments and derivatives of hyaluronic acid, heparin, fragments and derivatives of heparin, glycosamino glycan (GAG), GAG derivatives, polysaccharide, elastin, chitosan, alginate, or combinations thereof.

Examples of synthetic polymers (which may be used as a membrane) include, but are not limited to, nylon, polyacrylamide, polycarbonate, polyformaldehyde, polymethylmethacrylate, polytetrafluoroethylene, polytrifluorochlorethylene, polyvinylchloride, polyurethane, elastomeric organosilicon polymers, polyethylene, expanded polyethylene, polypropylene, polyurethane, polyglycolic acid, polyesters, polyamides, their mixtures, blends and copolymers are suitable as a membrane material. In one embodiment, said membrane is made from a class of polyesters such as polyethylene terephthalate including DACRON® and MYLAR® and polyaramids such as KEVLAR®, polyfluorocarbons such as polytetrafluoroethylene (PTFE) with and without copolymerized hexafluoropropylene (TEFLON® or GORE-TEX®), and porous or nonporous polyurethanes. In certain instances, the membrane comprises expanded fluorocarbon polymers (especially ePTFE) materials. Included in the class of preferred fluoropolymers are polytetrafluoroethylene (PTFE), fluorinated ethylene propylene (FEP), copolymers of tetrafluoroethylene (TFE) and perfluoro(propyl vinyl ether) (PFA), homopolymers of polychlorotrifluoroethylene (PCTFE), and its copolymers with TFE, ethylene-chlorotrifluoroethylene (ECTFE), copolymers of ethylene-tetrafluoroethylene (ETFE), polyvinylidene fluoride (PVDF), and polyvinylfluoride (PVF). Especially preferred, because of its widespread use in vascular prostheses, is ePTFE. In certain instances, the membrane comprises a combination of said materials listed above. In certain instances, the membrane is substantially impermeable to bodily fluids. Said substantially impermeable membrane can be made from materials that are substantially impermeable to bodily fluids or can be constructed from permeable materials treated or manufactured to be substantially impermeable to bodily fluids (e.g. by layering different types of materials described above or known in the art).

Additional examples of membrane materials include, but are not limited to, vinylidinefluoride/hexafluoropropylene hexafluoropropylene (HFP), tetrafluoroethylene (TFE), vinylidenefluoride, 1-hydropentafluoropropylene, perfluoro (methyl vinyl ether), chlorotrifluoroethylene (CTFE), pentafluoropropene, trifluoroethylene, hexafluoroacetone, hexafluoroisobutylene, fluorinated poly(ethylene-co-propylene (FPEP), poly(hexafluoropropene) (PHFP), poly(chlorotrifluoroethylene) (PCTFE), poly(vinylidene fluoride (PVDF), poly(vinylidene fluoride-co-tetrafluoroethylene) (PVDF-TFE), poly(vinylidene fluoride-co-hexafluoropropene) (PVDF-HFP), poly(tetrafluoroethylene-co-hexafluoropropene) (PTFE-HFP), poly(tetrafluoroethylene-co-vinyl alcohol) (PTFE-VAL), poly(tetrafluoroethylene-co-vinyl acetate) (PTFE-VAC), poly(tetrafluoroethylene-co-propene) (PTFEP) poly(hexafluoropropene-co-vinyl alcohol) (PHFP-VAL), poly(ethylene-co-tetrafluoroethylene) (PETFE), poly (ethylene-co-hexafluoropropene) (PEHFP), poly(vinylidene fluoride-co-chlorotrifluoroe-thylene) (PVDF-CTFE), and combinations thereof, and additional polymers and copolymers described in U.S. Publication 2004/0063805, incorporated by reference herein in its entirety for all purposes. Additional polyfluorocopolymers include tetrafluoroethylene (TFE)/perfluoroalkylvinylether (PAVE). PAVE can be perfluoromethylvinylether (PMVE), perfluoroethylvinylether (PEVE), or perfluoropropylvinylether (PPVE). Other polymers and copolymers include, polylactide, polycaprolacton-glycolide, polyorthoesters, polyanhydrides; polyaminoacids; polysaccharides; polyphosphazenes; poly (ether-ester) copolymers, e.g., PEO-PLLA, or blends thereof, polydimethyl-sioIxane; poly(ethylene-vingylacetate); acrylate based polymers or copolymers, e.g., poly (hydroxyethyl methylmethacrylate, polyvinyl pyrrolidinone; fluorinated polymers such as polytetrafluoroethylene; cellulose esters and any polymer and co-polymers.

The invention of this application has been described above both generically and with regard to specific embodiments. It will be apparent to those skilled in the art that various modifications and variations can be made in the embodiments without departing from the scope of the disclosure. Thus, it is intended that the embodiments cover the modifications and variations of this invention provided they come within the scope of the appended claims and their equivalents.

What is claimed is:

1. An apparatus comprising:
    a support structure including a plurality of absorbable filaments configured to support a tissue and degrade within a defined time period; and
    a membrane arranged about an entirety of the support structure including the plurality of absorbable filaments and an entirety of at least one of a proximal end and a distal end, the membrane configured to contain fragments of the plurality of absorbable filaments in response to a fracture or degradation of a filament, the membrane defining a first layer and a second layer, the plurality of absorbable filaments being arranged between layers of the membrane such that the first layer and the second layer of the membrane sandwich the plurality of absorbable filaments, wherein the proximal end is an integral portion of a proximal disk comprising a proximal expanded diameter portion such that the proximal end does not protrude beyond a proximal end of the proximal disk.

2. The apparatus of claim 1, wherein the membrane is configured to promote tissue growth and remain with the tissue after degradation of the absorbable f ilam ents.

3. The apparatus of claim 1, wherein the absorbable filaments are at least one of bio-absorbable and bio-corrodible.

4. The apparatus of claim 1, further including a proximal hub arranged at a proximal end of the plurality of absorbable filaments, a distal hub arranged at a distal end of the plurality of absorbable filaments, the proximal disk configured to contact a first side of a tissue wall, and a distal disk configured to contact a second side of a tissue wall.

5. The apparatus of claim 4, further including an elastic tensile member arranged coupled to the proximal hub and the distal hub and within the support structure, the elastic tensile member being configured to bring the proximal disk into apposition with the first side of the tissue wall and the distal disk into apposition with the second side of the tissue wall.

6. The apparatus of claim 4, further including a catch member arranged to, when engaged, connect the proximal hub and the distal hub within the support structure, the catch member being configured to bring the proximal disk into apposition with the first side of the tissue wall and the distal disk into apposition with the second side of the tissue wall.

7. The apparatus of claim 4, wherein the proximal hub includes proximal end portions of the plurality of absorbable filaments and the distal hub includes distal end portions of the plurality of absorbable filaments.

8. The apparatus of claim 7, wherein the proximal end portions of the plurality of absorbable filaments are formed together to form the proximal hub and the distal end portions of the plurality of absorbable filaments are formed together to define the distal hub.

9. The apparatus of claim 4, further comprising an intermediate hub including central portions of the plurality of absorbable filaments.

10. The apparatus of claim 9, wherein the intermediate hub includes a band of material arranged about the central portions of the plurality of absorbable filaments.

11. The apparatus of claim 4, wherein central portions of the plurality of absorbable filaments define a waist configured to form an open central area within the plurality of absorbable filaments.

12. The apparatus of claim 11, wherein the waist is configured to bring the proximal disk into apposition with the first side of the tissue wall and the distal disk into apposition with the second side of the tissue wall.

13. The apparatus of claim 1, wherein the membrane is configured to allow contact between the plurality of absorbable filaments and blood or moisture to facilitate degradation of the plurality of absorbable filaments.

14. The apparatus of claim 1, wherein the membrane includes a gap configured to allow direct tissue contact with the absorbable filaments.

15. The apparatus of claim 1, wherein the membrane is configured to facilitate movement of the plurality of absorbable filaments.

16. The apparatus of claim 1, wherein the plurality of absorbable filaments and the membrane are configured to facilitate crossing of an atrial septum after implantation.

17. The apparatus of claim 1, wherein at least one of the plurality of absorbable filaments includes a cross-section that is at least one of uneven, jagged, star-like, or polygonal.

18. The apparatus of claim 1, wherein the membrane is porous.

19. The apparatus of claim 18, wherein the plurality of filaments produce a degradation product as the plurality of filaments degrade, and wherein the membrane includes pores operable to allow the degradation product to pass through the pores once dimensions of the degradation product are reduced to a dimension at least as small as a dimension of the pores.

20. The apparatus of claim 1, wherein the support structure is tubular and is sandwiched between the first and second layers of the membrane so as to contain the plurality of filaments and/or fragments of the plurality of filaments therebetween.

21. The apparatus of claim 1, wherein the support structure is tubular having an inside and an outside, wherein a layer of membrane is adjacent the inside and the second layer of membrane is adjacent the outside so as to contain the plurality of filaments and/or fragments of the plurality of filaments therebetween.

22. The apparatus of claim 1, wherein the support structure is tubular and the filaments are sandwiched between the first and second layers of the membrane so as to contain the plurality of filaments and/or fragments of the plurality of filaments between the first and second layers of the membrane.

23. The apparatus of claim 1, wherein the membrane is configured to promote at least one of tissue ingrowth into the membrane and tissue encapsulation of at least a portion of the membrane.

24. A medical implantable occlusion device comprising:
a braiding of at least one absorbable filament said braiding having a deployed state and an elongated state and a proximal and distal end and the braiding comprising a proximal end hub, a proximal expanded diameter portion, a center portion, a distal expanded diameter portion, and a distal hub extending along a longitudinal axis in the deployed state and configured to be stretched into a tubular formation in the elongated state, the filament being helically wound and interwoven in multiple directions to allow for natural expansion, wherein the proximal end hub is an integral portion of the proximal expanded diameter portion such that the proximal end hub does not protrude beyond the proximal end of the medical implantable occlusion device; and
a membrane arranged about an entirety of the braiding and configured to contain fragments of the braid, the membrane defining a first layer and a second layer, the braiding arranged between the first layer and the second layer.

25. A method of treating an opening in a patient, the method comprising:
delivering a medical device within an opening at a treatment site, the medical device having a scaffold including a plurality of absorbable filaments arranged in a support structure having a first hub and a second hub with a waist extending therebetween, the scaffold configured to support a tissue and degrade within a defined time period and a membrane arranged about an entirety of the support structure including the plurality of absorbable filaments and an entirety of at least one of a proximal end and a distal end, the membrane defining a first layer and a second layer, the plurality of absorbable filaments contained between the first layer and the second layer, the medical device including an elastic tensile member arranged between the first and second hubs and within the waist, during deployment from an elongated state, a tensile forced in the elastic tensile member pulls the first and second hubs together;
degrading the plurality of filaments within the confines of the membrane;
containing fragments of the plurality of absorbable filaments within the membrane in response to the fracture or degradation of the plurality of filaments; and
maintaining the membrane within the opening after degradation of the plurality of filaments.

26. The method of claim 25, wherein containing fragments of the plurality of absorbable filaments includes lessening risk of liberating particulate degradation products.

27. The method of claim 25, wherein containing fragments of the plurality of absorbable filaments includes reducing adverse events caused by emboli in the vascular system.

28. An apparatus comprising:
a plurality of filaments defining an absorbable support structure configured to support a tissue and degrade within a defined time period, the absorbable support structure including central portion defining a waist, wherein the support structure includes a proximal end that is an integral portion of a proximal expanded diameter portion such that the proximal end of the support structure does not protrude beyond a proximal end of the proximal expanded diameter portion;
an intermediate hub surrounding the waist defined by the central portions of the plurality of filaments; and
a membrane arranged about an entirety of the absorbable structure including an entirety of at least one of a proximal end and a distal end, the membrane defining a first layer and a second layer, the absorbable structure being enclosed between layers of the membrane, the membrane configured to contain fragments of the absorbable structure in response to a fracture or degradation of at least a portion of the absorbable structure.

29. The apparatus of claim 28, wherein the absorbable structure is formed from a cut-tube, cut-sheet, filaments, an injection molding, or additive printing.

30. The apparatus of claim 28, wherein the absorbable structure and the membrane are configured to implant within vasculature or appendage of a patient.

31. The apparatus of claim 28, further comprising a plug arranged at one end of the absorbable structure.

32. The apparatus of claim 28, wherein the membrane is at least partially absorbable and configured to facilitate tissue growth.

* * * * *

UNITED STATES PATENT AND TRADEMARK OFFICE
CERTIFICATE OF CORRECTION

PATENT NO. : 11,911,272 B2
APPLICATION NO. : 16/745831
DATED : February 27, 2024
INVENTOR(S) : Michael C. Chan et al.

It is certified that error appears in the above-identified patent and that said Letters Patent is hereby corrected as shown below:

In the Claims

Column 24 Line 13 "f ilam ents" should read --filaments--.

Signed and Sealed this
Sixth Day of August, 2024

Katherine Kelly Vidal
*Director of the United States Patent and Trademark Office*